(12) United States Patent
Marchese et al.

(10) Patent No.: US 9,827,292 B2
(45) Date of Patent: Nov. 28, 2017

(54) USE OF KGF IN THE TREATMENT OF MENOPAUSAL DISORDERS

(71) Applicant: Università degli Studi di Roma "La Sapienza", Rome (IT)

(72) Inventors: Cinzia Marchese, Rome (IT); Simona Ceccarelli, Rome (IT); Antonio Angeloni, Rome (IT)

(73) Assignee: UNIVERSITA DEGLI STUDI DI ROMA "LA SAPIENZA", Rome (IT)

( * ) Notice: Subject to any disclaimer, the term of this patent is extended or adjusted under 35 U.S.C. 154(b) by 0 days.

(21) Appl. No.: 14/419,993

(22) PCT Filed: Aug. 7, 2013

(86) PCT No.: PCT/EP2013/066560
§ 371 (c)(1),
(2) Date: Feb. 6, 2015

(87) PCT Pub. No.: WO2014/023773
PCT Pub. Date: Feb. 13, 2014

(65) Prior Publication Data
US 2015/0224172 A1    Aug. 13, 2015

(30) Foreign Application Priority Data
Aug. 9, 2012 (IT) .............................. RM2012A0404

(51) Int. Cl.
| | |
|---|---|
| A61K 45/08 | (2006.01) |
| A61K 47/04 | (2006.01) |
| A61K 38/18 | (2006.01) |
| A61K 47/34 | (2017.01) |

(52) U.S. Cl.
CPC .......... *A61K 38/1825* (2013.01); *A61K 38/18* (2013.01); *A61K 47/34* (2013.01)

(58) Field of Classification Search
None
See application file for complete search history.

(56) References Cited

U.S. PATENT DOCUMENTS 6,416,779 B1 * 7/2002 D'Augustine ............ A61F 6/08
424/430

OTHER PUBLICATIONS

Pandit et al Am J Med Sci. Oct. 1997;314(4):228-31. Postmenopausal vaginal atrophy and atrophic vaginitis.*
Yan et al Science. Oct. 20, 2000;290(5491):523-7.Two-amino acid molecular switch in an epithelial morphogen that regulates binding to two distinct receptors.*
Ngo, in the Protein Folding Problem and Tertiary Structure Prediction, Merz et al. (eds.), Birkhauser Boston: Boston, MA, pp. 433 and 492-495, 1994.*
Bowie, Science Mar. 16, 1990: vol. 247 No. 4948 pp. 1306-1310 Deciphering the message in protein sequences: tolerance to amino acid substitutions.*
Ceccarelli et al., Potential dual role of KGF/KGFR as a target option in novel therapeutic strategies for the treatment of cancers and mucosal damages Expert Opin. Ther. Targets (2012) 16(4):377-393.*
Rotolo et al., Silencing of Keratinocyte Growth Factor Receptor Restores 5-Fluorouracil and Tamoxifen Efficacy on Responsive Cancer Cells PLoS ONEJun. 2008 | vol. 3 | Issue 6 | e2528 pp. 1-15.*
Ceccarelli et al Topical KGF treatment as a therapeutic strategy for vaginal atrophy in a model of ovariectomized mice J. Cell. Mol. Med. vol. 18, No. 9, 2014 pp. 1895-1907.*
Uterine serous carcinomaUterine serous carcinoma—Wikipedia, the free encyclopedia pp. 1-4, downloaded Mar. 11, 2016.*
Tamoxifen From Wikipedia, the free encyclopedia pp. 1-14, downloaded Mar. 11, 2016.*
Kimchi-Sarfaty Cet al., A "silent" polymorphism in the MDR1 gene changes substrate specificity.Science. Jan. 26, 2007;315(5811):525-8.*
Voet, Biochemistry John Wiley and Sons, 1990, pp. 126-128.*
NCBI search for keratinocyte growth factor pp. 1-3, downloaded Mar. 24, 2017.*
Tamoxifen From Wikipedia, the free encyclopedia pp. 1-2 , downloaded Mar. 24, 2017.*
Masui, F., et al: "Involvement of keratinocyte growth factor (KGF)-KGF receptor signaling in developmental estrogenization syndrome of mouse vagina", Cell and Tissue Research, vol. 318, No. 3, Dec. 1, 2004 (Dec. 1, 2004), pp. 591-598, abstract, p. 591, col. 2, paragraph 4.
Hom, Y. K., et al: "Keratinocyte Growth Factor (KGF) Injected Into Female Mouse Neonates Stimulates Uterine and Vaginal Epithelial Growth", Molecular Biology of the Cell, American Society for Cell Biology, US, vol. 7, No. Suppl, Dec. 7, 1996 (Dec. 7, 1996), p. 312A, p. 377, col. 1, paragraph 2.
Slayden, O., et al: "Keratinocyte Growth Factor (KGF) Stimulates Epithelial Cell Proliferation in the Primate Oviduct and Vagina", Biology of Reproduction, Supplement, Champaign, IL, US, vol. 56, No. Suppl. 01, Aug. 2, 1997 (Aug. 2, 1997), p. 103, the whole document.
Raja Raja: "Wound re-epithelialization: modulating kerationcyte migration in wound healing", Frontiers in Bioscience, vol. 12, No. 8-12, Jan. 1, 2007 (Jan. 1, 2007), p. 2849, p. 2251, col. 1, paragraph 3.
Finch, P. W., et al: "Keratinocyte growth factor/ fibroblast growth factor 7, a homeostatic factor with therapeutic potential for epithelial protection and repair", Advances in Cancer Research, Academic Press, US , vol. 91, Jan. 1, 2004 (Jan. 1, 2004), pp. 69-136, the whole document.
Anonymous: "Vaginal atrophy, DS00770", Mayo Clinic, Sep. 17, 2010 (Sep. 17, 2010), pp. 1-3, Retrieved from the Internet: URL: http://www.mayoclinic.com/health/vaginal-atrophy/DS00770/METHOD=print&DSECTION=all [retrieved on Mar. 6, 2013], p. 2, paragraph 14-p. 3, paragraph 3.

(Continued)

*Primary Examiner* — Maria Leavitt
(74) *Attorney, Agent, or Firm* — Lucas & Mercanti, LLP

(57) ABSTRACT

The present invention relates to the use of keratinocyte growth factor (KGF/FGF7) and pharmaceutical compositions thereof in the treatment of vaginal atrophy, dysuria, vaginal pain and/or vaginal dryness induced by a post-menopausal state, by surgical intervention, by illness and/or by chemotherapy or radiotherapy treatments.

6 Claims, 12 Drawing Sheets

(56) References Cited

OTHER PUBLICATIONS

Anonymous: "Painful urination (dysuria), MY00734", Mayo Clinic, Aug. 20, 2011 (Aug. 20, 2011), pp. 1-1, Retrieved from the Internet: URL: http://www.mayoclinic.com/health/painful-urination/MY00734/METHOD=print [retrieved on Mar. 6, 2013], the whole document.

Anonymous: Vaginal dryness, DS00550, Myo Clinic, Jul. 1, 2010 (Jul. 1, 2010), pp. 1-3, Retrieved from the Internet: URL: http://web.archive.org/web/20121023103403/http://www.mayoclinic.com/health/vaginal-dryness/DS00550/METHOD=print [retrieved on Mar. 6, 2013], p. 2, paragraph 10-p. 3, paragraph 2.

P. B. Panici, et al: "Vaginoplasty using autologous in vitro cultured vaginal tissue in a patient with Mayer-von-Rokitansky-Kuster-Hauser syndrome", Human Reproduction, vol. 22, No. 7, Jul. 1, 2007 (Jul. 1, 2007), pp. 2025-2028, the whole document.

\* cited by examiner

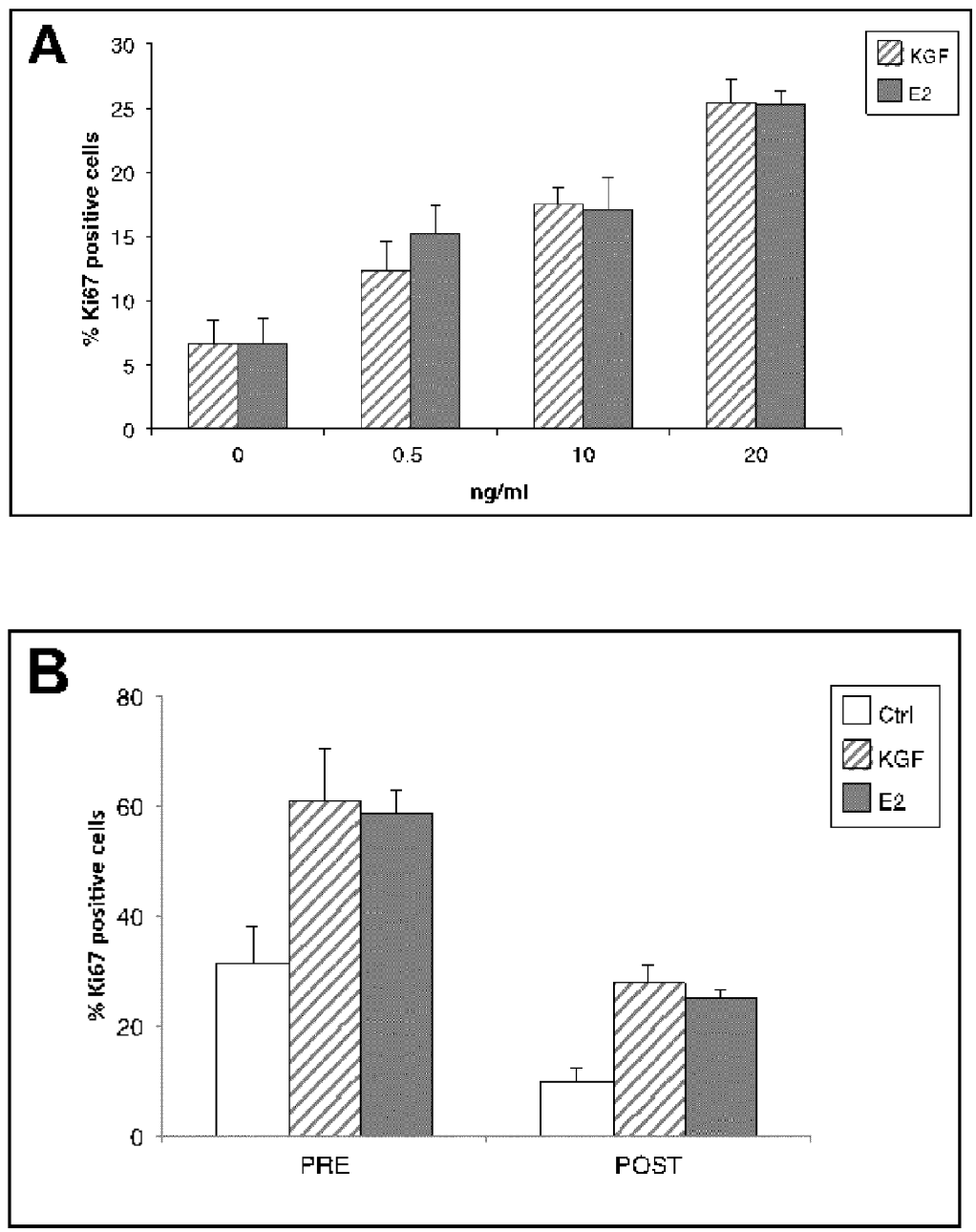
Fig. 1 (1/2)

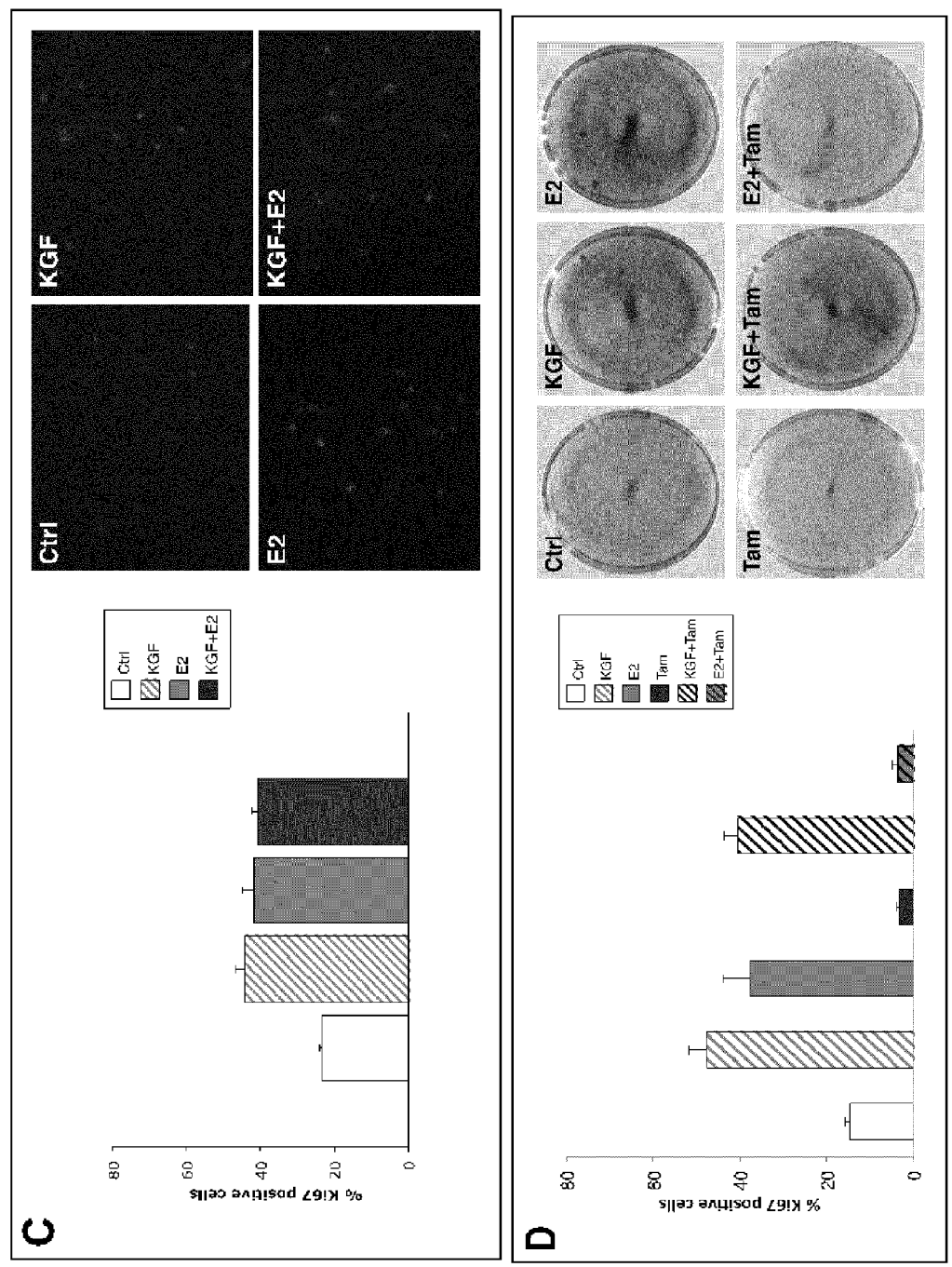
Fig. 1 (2/2)

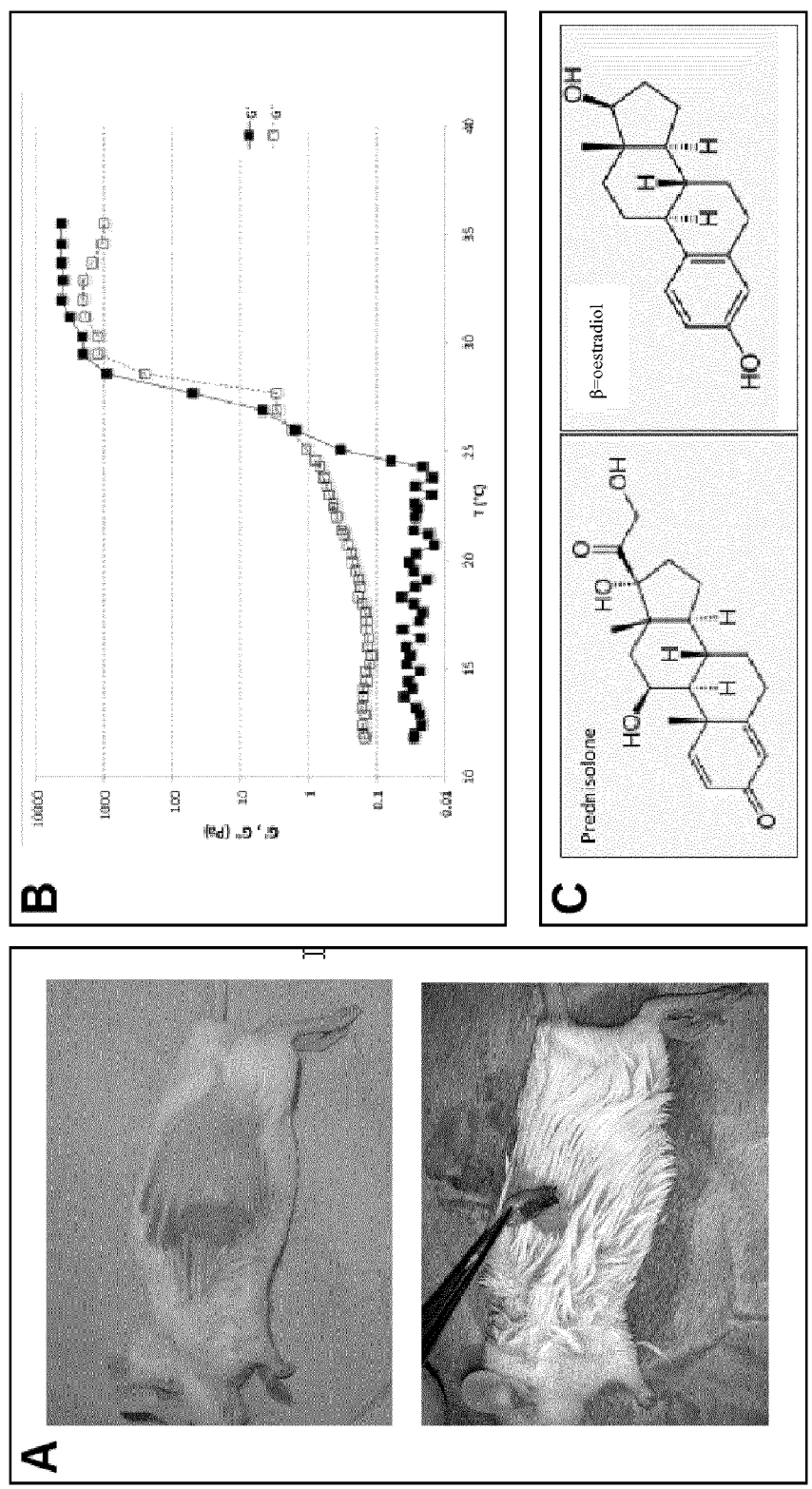
Fig. 6 (1/2)

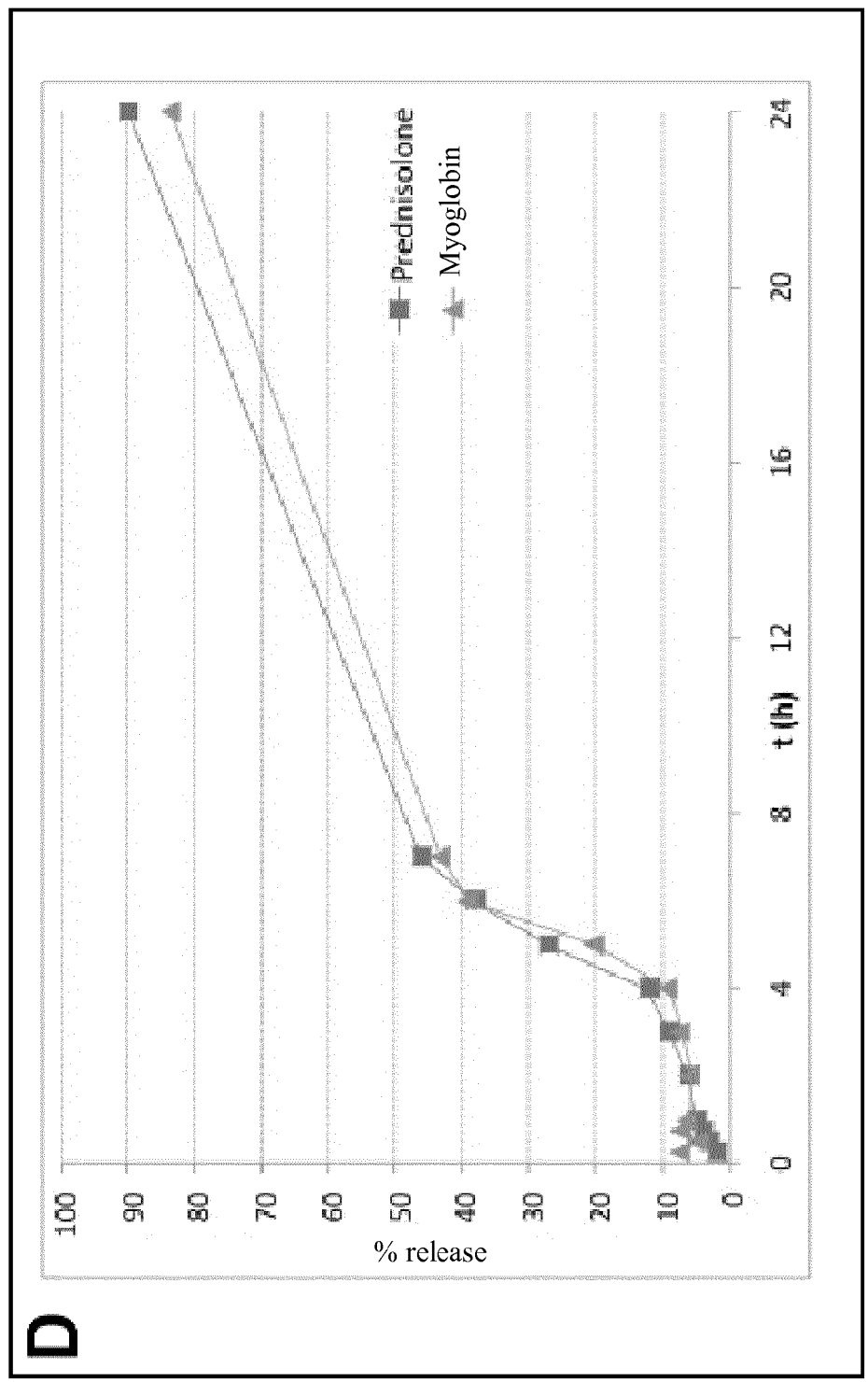
Fig 6 (2/2)

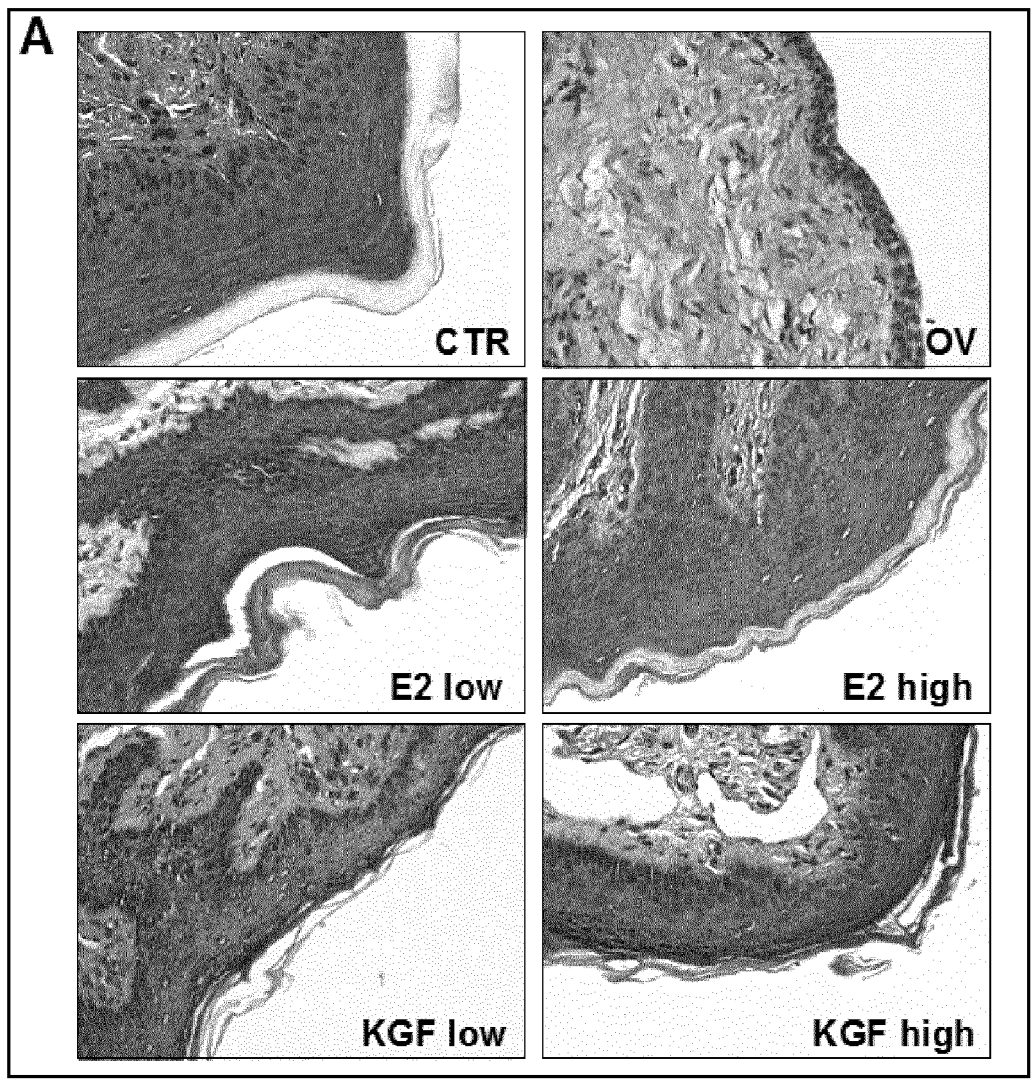
Fig. 8 (1/2)

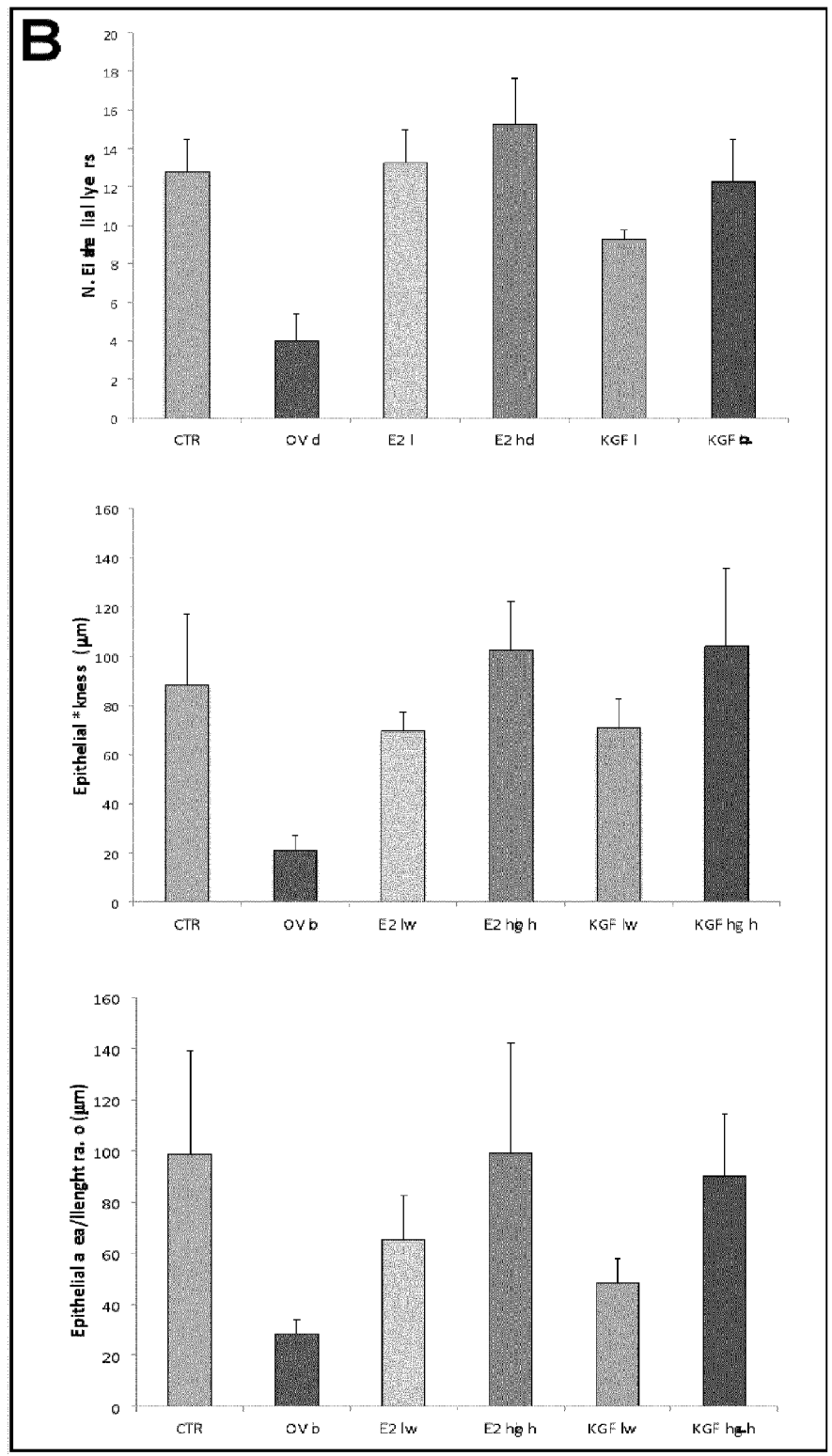
Fig. 8 (2/2)

SEQUENCE LISTING

<160> NUMBER OF SEQ ID NOS: 6

<210> SEQ ID NO 1
<211> LENGTH: 3936
<212> TYPE: DNA
<213> ORGANISM: Homo sapiens

<400> SEQUENCE: 1

```
agttttaatt gcttccaatg aggtcagcaa aggtatttat cgaaaagccc tgaataaaag      60
gctcacacac acacacaagc acacacgcgc tcacacacag agagaaaatc cttctgcctg     120
```

-continued

```
ttgatttatg gaaacaatta tgattctgct ggagaacttt tcagctgaga aatagtttgt      180
agctacagta gaaaggctca agttgcacca ggcagacaac agacatggaa ttcttatata      240
tccagctgtt agcaacaaaa caaaagtcaa atagcaaaca gcgtcacagc aactgaactt      300
actacgaact gtttttatga ggatttatca acagagttat ttaaggagga atcctgtgtt      360
gttatcagga actaaaagga taaggctaac aatttggaaa gagcaactac tctttcttaa      420
atcaatctac aattcacaga taggaagagg tcaatgacct aggagtaaca atcaactcaa      480
gattcatttt cattatgtta ttcatgaaca cccggagcac tacactataa tgcacaaatg      540
gatactgaca tggatcctgc caactttgct ctacagatca tgctttcaca ttatctgtct      600
agtgggtact atatctttag cttgcaatga catgactcca gagcaaatgg ctacaaatgt      660
gaactgttcc agccctgagc gacacacaag aagttatgat tacatggaag agggggatat      720
aagagtgaga agactcttct gtcgaacaca gtggtacctg aggatcgata aaagaggcaa      780
agtaaaaggg acccaagaga tgaagaataa ttacaatatc atggaaatca ggacagtggc      840
agttggaatt gtggcaatca aagggtgga aagtgaattc tatcttgcaa tgaacaagga       900
aggaaaactc tatgcaaaga aagaatgcaa tgaagattgt aacttcaaag aactaattct      960
ggaaaaccat tacaacacat atgcatcagc taaatggaca cacaacggag gggaaatgtt     1020
tgttgcctta aatcaaaagg ggattcctgt aagaggaaaa aaaacgaaga agaacaaaa      1080 aacagcccac tttcttccta tggcaataac ttaattgcat atggtatata aagaaccagt     1140
tccagcaggg agatttcttt aagtggactg ttttctttct tctcaaaatt ttctttcctt     1200 ttattttta gtaatcaaga aaggctggaa aactactgaa aaactgatca agctggactt      1260
gtgcatttat gtttgtttta agacactgca ttaagaaag atttgaaaag tatacacaaa      1320
aatcagattt agtaactaaa ggttgtaaaa aattgtaaaa ctggttgtac aatcatgatg     1380
ttagtaacag taatttttt cttaaattaa tttaccctta agagtatgtt agatttgatt      1440
atctgataat gattatttaa atattcctat ctgcttataa aatggctgct ataataataa      1500
taatacagat gttgttatat aaggtatatc agacctacag gcttctggca ggatttgtca     1560
gataatcaag ccacactaac tatggaaaat gagcagcatt ttaaatgctt tctagtgaaa     1620
aattataatc tacttaaact ctaatcagaa aaaaaattct caaaaaaact attatgaaag     1680
tcaataaaat agataattta acaaaagtac aggattagaa catgcttata cctataaata     1740
agaacaaaat ttctaatgct gctcaagtgg aaagggtatt gctaaaagga tgtttccaaa     1800
aatcttgtat ataagatagc aacagtgatt gatgataata ctgtacttca tcttacttgc     1860
cacaaaataa cattttataa atcctcaaag taaaattgag aaatctttaa gttttttca     1920 agtaacataa tctatctttg tataattcat atttgggaat atggcttta ataatgttct      1980 tcccacaaat aatcatgctt ttttcctatg gttacagcat taaactctat tttaagttgt     2040
ttttgaactt tattgttttg ttatttaagt ttatgttatt tataaaaaa aaaccttaat      2100 aagctgtatc tgtttcatat gcttttaatt ttaaggaat acaaaactg tctggctcaa      2160 cggcaagttt ccctcccttt tctgactgac actaagtcta gcacacagca cttgggccag     2220
caaatcctgg aaggcagaca aaaataagag cctgaagcaa tgcttacaat agatgtctca     2280
cacagaacaa tacaaatatg taaaaaatct ttcaccacat attcttgcca attaattgga     2340
tcatataagt aaaatcatta caaatataag tatttacagg attttaaagt tagaatatat     2400
ttgaatgcat gggtagaaaa tatcatattt taaaactatg tatatttaaa tttagtaatt     2460
ttctaatctc tagaaatctc tgctgttcaa aaggtggcag cactgaaagt tgttttcctg     2520
```

```
ttagatggca agagcacaat gcccaaaata gaagatgcag ttaagaataa ggggccctga   2580
atgtcatgaa ggcttgaggt cagcctacag ataacaggat tattacaagg atgaatttcc   2640
acttcaaaag tctttcattg gcagatcttg gtagcacttt atatgttcac caatgggagg   2700
tcaatattta tctaatttaa aaggtatgct aaccactgtg gttttaattt caaaatattt   2760
gtcattcaag tcccttaca taaatagtat ttggtaatac atttatagat gagagttata   2820
tgaaaaggct aggtcaacaa aaacaataga ttcatttaat tttcctgtgg ttgacctata   2880
cgaccaggat gtagaaaact agaaagaact gcccttcctc agatatactc ttgggagaga   2940
gcatgaatgg tattctgaac tatcacctga ttcaaggact tgctagcta ggttttgagg   3000 tcaggcttca gtaactgtag tcttgtgagc atattgaggg cagaggagga cttagttttt   3060
catatgtgtt tccttagtgc ctagcagact atctgttcat aatcagtttt cagtgtgaat   3120
tcactgaatg tttatagaca aaagaaaata cacactaaaa ctaatcttca ttttaaaagg   3180
gtaaaacatg actatacaga aatttaaata gaaatagtgt atatacatat aaaatacaag   3240
ctatgttagg accaaatgct ctttgtctat ggagttatac ttccatcaaa ttacatagca   3300
atgctgaatt aggcaaaacc aacatttagt ggtaaatcca ttcctggtag tataagtcac   3360 ctaaaaaga cttctagaaa tatgtacttt aattatttgt ttttctccta tttttaaatt   3420
tattatgcaa attttagaaa ataaaatttg ctctagttac acaccttag aattctagaa   3480 tattaaaact gtaaggggcc tccatccctc ttactcattt gtagtctagg aaattgagat   3540
tttgatacac ctaaggtcac gcagctgggt agatatacag ctgtcacaag agtctagatc   3600
agttagcaca tgctttctac tcttcgatta ttagtattat tagctaatgg tctttggcat   3660 gttttttgttt tttatttctg ttgagatata gcctttacat ttgtacacaa atgtgactat   3720
gtcttggcaa tgcacttcat acacaatgac taatctatac tgtgatgatt tgactcaaaa   3780
ggagaaaaga aattatgtag ttttcaattc tgattcctat tcacctttg tttatgaatg   3840 gaaagctttg tgcaaaatat acatataagc agagtaagcc ttttaaaaat gttctttgaa   3900
agataaaatt aaatacatga gtttctaaca attaga                            3936
```

<210> SEQ ID NO 2
<211> LENGTH: 194
<212> TYPE: PRT
<213> ORGANISM: Homo sapiens

<400> SEQUENCE: 2

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
```

```
            115                 120                 125
Ala Lys Lys Glu Cys Asn Glu Asp Cys Asn Phe Lys Glu Leu Ile Leu
        130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 3
<211> LENGTH: 194
<212> TYPE: PRT
<213> ORGANISM: Homo sapiens

<400> SEQUENCE: 3

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
        130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 4
<211> LENGTH: 21
<212> TYPE: DNA
<213> ORGANISM: Artificial Sequence
<220> FEATURE:
<223> OTHER INFORMATION: synthetic primer

<400> SEQUENCE: 4
ggctctgttc aatgtgaccg a                                              21

<210> SEQ ID NO 5
<211> LENGTH: 24
<212> TYPE: DNA
<213> ORGANISM: Artificial Sequence
```

```
<220> FEATURE:
<223> OTHER INFORMATION: synthetic primer

<400> SEQUENCE: 5
gttggcctgc cctatataat tgga                                          24

<210> SEQ ID NO 6
<211> LENGTH: 16
<212> TYPE: DNA
<213> ORGANISM: Artificial Sequence
<220> FEATURE:
<223> OTHER INFORMATION: synthetic primer

<400> SEQUENCE: 6
ttccccagca tccgcc                                                    16
```

USE OF KGF IN THE TREATMENT OF MENOPAUSAL DISORDERS

CROSS-REFERENCE TO RELATED APPLICATIONS

This application is a 371 of PCT/EP2013/066560, filed Aug. 7, 2013, which claims the benefit of European Patent Application No. RM2012A000404, filed Aug. 9, 2012.

FIELD OF THE INVENTION

The present invention concerns the medical field, and in particular relates to the use of keratinocyte growth factor (KGF/FGF7) and pharmaceutical compositions thereof in the treatment of vaginal atrophy, dysuria, vaginal pain and/or vaginal dryness induced by a post-menopausal state, by surgical intervention, by illness and/or by chemotherapy or radiotherapy treatments.

BACKGROUND OF THE INVENTION

The lack of oestrogens in post-menopause causes alterations to the vaginal epithelium in more then 50% of women aged between 50 and 60 years [Pandit et al, 1997]. These disorders are characterised by their chronicity and recurrence, sometimes also accompanied by consequent sexual dysfunction, and their significance easily surpasses their actual severity in as much as they reinforce the fear of a general decline [Rossin-Amar, 2000]. The lack of oestrogens causes progressive atrophy of the vulva, which results in a gradual breakdown of the mucus, with 30-50% reduction of vascularisation levels. The simultaneous reduction of glycogen, in particular in cells of the intermediate stratum, causes a change to the vaginal ecosystem, with a consequent increased risk of the presence of pathogenic agents responsible for recurrent vaginitides. In addition, vaginal atrophy can also occur in pre-menopausal women who have undergone a surgical intervention due to endometrial cancer, including pelvic cancer, or paraaortic lymphadenectomy and are treated with adjuvant vaginal brachytherapy (VBT) in order to reduce the risk of local relapses and to improve the survival rate of patients [Scholten 2005; Keys 2004; Lee 2006]. All of these treatments can give rise to adverse effects in a variable percentage of patients, including dysuria, vaginal pain, atrophy of the vaginal mucus, and vaginal dryness [Dickler 2010]. These symptoms can be considered a significant health problem for a considerable part of the global female population, since they are often linked to inflammation, dyspareunia and loss of sexual enjoyment.

The loss of oestrogens is recognised as the most common cause of the symptoms of the menopause, often causing the treatment of post-menopausal vulvo-vaginal disorders with systemic hormone replacement therapy (HRT). However, the involvement of oestrogens in the genesis and progression of tumours of the endometrium, ovary and breast, even though the increased risk of cancer depends on the type of hormone replacement therapy, the duration of use, body mass and the period between menopause and the onset of the hormone replacement therapy, leads to scepticism among women and also to reluctance among some doctors to advise the adjuvant therapy [Hendrix et al, 2005; Grodstein et al, 2004], which has been placed seriously in doubt. Until now, no agreement has been reached in respect of the suitable therapy: HRT must be administered to women suffering from menopausal disorders in order to satisfy their individual needs, taking into account their individual risk profile and the general therapeutic objectives.

For these reasons, formulations of intravaginal oestrogens have been introduced in order to avoid systemic exposure to oestrogens and have been preferred in women who have no other menopausal symptoms requiring systemic treatment [Johnston et al, 2004; Willhite and O'Connell, 2011]. However, it has been demonstrated that topical oestradiol is significantly absorbed and appears in the general circulation [Martin et al, 1979; Furuhjelm et al, 1980; Deutsch et al, 1981; Mandel et al, 1983; Ballag, 2005; Kendall et al, 2006; Kvorning and Jensen, in: Publication Presented at: International workshop, Copenhagen, 1986], thus confirming the exposure to the increased risk of breast cancer and endometrial cancer after local hormone treatment [Notelovitz et al, 2002; Rioux et al, 2000; Schiff et al, 1977]. In light of this consideration, non-hormonal preparations have been developed for the treatment of vaginal atrophy [Kendall et al, 2006; Berger et al, 2008], such as isoflavones derived from soy. However, the use of topical formulations based on soy isoflavones for the purpose of preventing post-menopausal symptoms has provided insufficient results in terms of efficacy [Levis et al, 2011].

The oestrogen receptor alpha (ERα) performs its function predominantly via binding to its ligand, 17β oestradiol (E2), which induces conformational changes that allow the recruitment of coactivator molecules and the binding to oestrogen response elements (EREs) on the DNA to control the transcription of target genes ("classic" signal pathway of the ER). In the last decade, emerging tests have supported the importance of an alternative signal pathway of ERα (referred to as a "non-classic" path) in mediating the actions of oestrogens [Hall et al, 2001].

This path can bring genotropic effects in target cells and is independent of the binding between ER and ERE. The genotropic signal mediated by ERα involves other transcription factors, such as the activator protein 1 (AP1), the specificity protein 1 (SP1), and NF-κB [Paech et al, 1997; Coleman and Smith, 2001; Porter et al, 1996; Cerillo et al, 1998], which in turn mediate the regulation of the transcription of their target genes. The genotropic signal mediated from ERα includes the activation of the membrane-associated receptor and the stimulation of cytoplasmic pathways, such as PI3K/AKT, ERK and the signalling cascade of p38 [Singh, 2001; Watters et al, 1997; Zhou et al, 1996]. It is interesting to note that the factors determining whether the signal mediated from ER passes via the classic pathway or via the non-classic pathway, remain virtually unknown.

In recent years, it has been demonstrated that various growth factors play a role in the proliferation of cancerous cells of the breast, interacting with the pathway of the oestrogens, although the mechanisms and the effects of such interaction are not yet clear. A certain number of studies have produced suggestions of a cross-talk between the signalling of ER and the signalling of EGF/EGFR. In particular, it has been hypothesised that the development of resistance to tamoxifen in breast cancer cells can be correlated with the ER-mediated activation of EGFR, HER2/neu and IGFR.

Keratinocyte growth factor (KGF/FGF7) (NCBI Reference Sequence NM_002009.3, GenBank amino acid sequence: CAG46799.1), a member of the family of fibroblast growth factors (FGFs), plays a fundamental role in the regulation of cell proliferation, migration and differentiation during development and in response to damage and repair of tissues [Finch and Rubin, 2004]. It acts by binding to the receptor tyrosine kinase FGFR2-IIIb/KGFR, generated by means of alternative splicing of the FGFR2 gene and expressed predominantly on the epithelial cells of various organs, playing a key role in the control of epithelial growth and differentiation [Zhang et al, 2006]. The KGF/KGFR pathway is essential to maintain the integrity and function of adult epithelial cells due to the cytoprotective and regenerative effect of KGF. In fact, the expression of KGF is strongly over-regulated after lesions in various epithelial tissues, such as skin, kidneys, bladder, pancreas, stomach and intestine [Werner et al, 1992; Marchese et al, 1995; Brauchle et al, 1996; Werner, 1998]. In addition, KGF protects against lesions of the pulmonary epithelium and improves the distal repair of the airways, stimulating cell proliferation, inhibiting apoptosis and the free oxygen radicals, and mobilising epithelial progenitor cells [Gomperts et al, 2007].

It has been demonstrated that treatment with recombinant KGF (palifermin) is able to protect epithelial cells against a variety of lesions, including damage induced by radiation, and KGF has therefore been approved by the FDA for the treatment of severe oral mucositis resulting from the radiotherapy and/or chemotherapy of cancer in patients with haematological or head or neck tumours [Spielberger et al, 2004; Beaven and Shea, 2007; Brizel et al, 2008; Barash et al, 2009]. On the other hand, the administration of KGF to mice with developing vaginas during the neonatal period results in oestrogen growth, independently of the vaginal epithelium, thus suggesting a potential link between treatment with oestrogens and activation of the signal of KGF/KGFR [Masui et al, 2004]. In addition, the authors have already carried out the first autologous transplant of vaginal tissue in a woman suffering from Mayer Rokitansky Kuster Hauser syndrome (MRKHS) by means of the use of autologous vaginal tissue cultivated in vitro [Panici et al, 2007], thus forming the ideal model in vitro to analyse the effect of oestrogens and KGF on the trophism of the vaginal mucus.

International application WO 2006/083087 describes that the N-terminal peptide AIMP1 is able to stimulate synthesis of collagen and/or expression of KGF. However, the ability of the peptide to pass through the epidermal layer and the plasma membrane and to therefore be truly effective in cutaneous treatments has not been demonstrated. As is instead known in literature, the protein substances do not pass through the epidermal layer in the presence of undamaged skin.

There is thus a need to provide a therapeutic agent able to locally treat menopausal disorders, including vaginal dryness and atrophy, substituting the therapies already in use (formulations based on oestrogens).

SUMMARY OF THE INVENTION

The authors have investigated the cross-talk between oestrogen precursors and KGFR in order to clarify the mechanisms at the root of the effect of oestrogens that promotes growth and the potential role of growth factors in the development of new therapeutic strategies for mucosal atrophy. In addition, the authors have compared the in vivo efficacy of local treatment with oestrogens with topical administration of KGF, demonstrating that KGF can be used as alternative therapy for post-menopausal vaginal atrophy or other dysfunctions, such as those that occur in patients subjected to radiotherapy after surgery for endometrial cancer.

It is indicated that vaginal atrophy (atrophic vaginitis) is defined as a thinning and inflammation of the vaginal walls due to a decline in estrogen. Less circulating estrogen makes vaginal tissues thinner, drier, less elastic and more fragile. Moreover, genital function is closely related to urinary system function. In fact, vaginal atrophy symptoms include vaginal dryness, vaginal burning, burning with urination, urgency with urination, more urinary tract infections, urinary incontinence, light bleeding after intercourse, discomfort with intercourse and shortening and tightening of the vaginal canal. These symptoms which include dysuria and vaginal pain are closely and directly related to thinning of vaginal mucosa. Therefore, the positive effect of KGF on vaginal epithelium trophism observed in the present invention represent a successfully treatment for these symptoms, in particular when they are subsequent to vaginal atrophy.

In the present invention, it was unexpectedly found that KGF can successfully treat vaginal atrophy. In particular, the unexpected technical effect of KGF in the treatment of vaginal atrophy is observed after topical use and at very low doses (0.4 micrograms/ml and 1.2 micrograms/ml corresponding respectively to 10 ng/25 ul and 30 ng/25 ul). Moreover, the authors demonstrated that KGF in vivo effect is better than that of E2, since the same increase in epithelial thickness can be obtained by using KGF at 30 ng/25 ul and E2 at 1 ug/25 ul (see FIG. 8B). Finally, they demonstrated that KGF was not only able to counteract vaginal thinning by stimulating epithelial cells proliferation but also to restore epithelium lubrication through stimulation of mucinous cells (see FIG. 9B).

The invention therefore relates to keratinocyte growth factor (KGF/FGF7), orthologs, derivatives and fragments thereof for use in the treatment of vaginal atrophy, vaginal pain and/or vaginal dryness caused by a post-menopausal state, a surgical intervention, an illness and/or by chemotherapy or radiotherapy treatments.

The term "keratinocyte growth factor" or "KGF/FGF7" or "KGF" means the entire wild protein KGF (NCBI reference Sequence: NM_002009.3 (SEQ ID No. 1):

AGTTTTAATTGCTTCCAATGAGGTCAGCAAAGGTATTTATCGAAAAGC

CCTGAATAAAAGGCTCACACACACACACAAGCACACACGCGCTCACAC

ACAGAGAGAAAATCCTTCTGCCTGTTGATTTATGGAAACAATTATGAT

TCTGCTGGAGAACTTTTCAGCTGAGAAATAGTTTGTAGCTACAGTAGA

AAGGCTCAAGTTGCACCAGGCAGACAACAGACATGGAATTCTTATATA

TCCAGCTGTTAGCAACAAAACAAAAGTCAAATAGCAAACAGCGTCACA

GCAACTGAACTTACTACGAACTGTTTTTATGAGGATTTATCAACAGAG

TTATTTAAGGAGGAATCCTGTGTTGTTATCAGGAACTAAAAGGATAAG

GCTAACAATTTGGAAAGAGCAACTACTCTTTCTTAAATCAATCTACAA

TTCACAGATAGGAAGAGGTCAATGACCTAGGAGTAACAATCAACTCAA

GATTCATTTTCATTATGTTATTCATGAACACCCGGAGCACTACACTAT

AATGCACAAATGGATACTGACATGGATCCTGCCAACTTTGCTCTACAG

ATCATGCTTTCACATTATCTGTCTAGTGGGTACTATATCTTTAGCTTG

CAATGACATGACTCCAGAGCAAATGGCTACAAATGTGAACTGTTCCAG

CCCTGAGCGACACACAAGAAGTTATGATTACATGGAAGGAGGGGATAT

AAGAGTGAGAAGACTCTTCTGTCGAACACAGTGGTACCTGAGGATCGA

TAAAAGAGGCAAAGTAAAAGGGACCCAAGAGATGAAGAATAATTACAA

TATCATGGAAATCAGGACAGTGGCAGTTGGAATTGTGGCAATCAAAGG

```
GGTGGAAAGTGAATTCTATCTTGCAATGAACAAGGAAGGAAAACTCTA
TGCAAAGAAAGAATGCAATGAAGATTGTAACTTCAAAGAACTAATTCT
GGAAAACCATTACAACACATATGCATCAGCTAAATGGACACACAACGG
AGGGGAAATGTTTGTTGCCTTAAATCAAAAGGGGATTCCTGTAAGAGG
AAAAAAAACGAAGAAAGAACAAAAAACAGCCCACTTTCTTCCTATGGC
AATAACTTAATTGCATATGGTATATAAAGAACCAGTTCCAGCAGGGAG
ATTTCTTTAAGTGGACTGTTTTCTTTCTTCTCAAAATTTTCTTTCCTT
TTATTTTTTAGTAATCAAGAAAGGCTGGAAAACTACTGAAAACTGAT
CAAGCTGGACTTGTGCATTTATGTTTGTTTTAAGACACTGCATTAAAG
AAAGATTTGAAAAGTATACACAAAAATCAGATTTAGTAACTAAAGGTT
GTAAAAAATTGTAAAACTGGTTGTACAATCATGATGTTAGTAACAGTA
ATTTTTTTCTTAAATTAATTTACCCTTAAGAGTATGTTAGATTTGATT
ATCTGATAATGATTATTTAAATATTCCTATCTGCTTATAAAATGGCTG
CTATAATAATAATAATACAGATGTTGTTATATAAGGTATATCAGACCT
ACAGGCTTCTGGCAGGATTTGTCAGATAATCAAGCCACACTAACTATG
GAAAATGAGCAGCATTTTAAATGCTTTCTAGTGAAAAATTATAATCTA
CTTAAACTCTAATCAGAAAAAAATTCTCAAAAAACTATTATGAAAG
TCAATAAAATAGATAATTTAACAAAAGTACAGGATTAGAACATGCTTA
TACCTATAAATAAGAACAAAATTTCTAATGCTGCTCAAGTGGAAAGGG
TATTGCTAAAAGGATGTTTCCAAAAATCTTGTATATAAGATAGCAACA
GTGATTGATGATAATACTGTACTTCATCTTACTTGCCACAAAATAACA
TTTTATAAATCCTCAAAGTAAAATTGAGAAATCTTTAAGTTTTTTTCA
AGTAACATAATCTATCTTTGTATAATTCATATTTGGGAATATGGCTTT
TAATAATGTTCTTCCCACAAATAATCATGCTTTTTTCCTATGGTTACA
GCATTAAACTCTATTTTAAGTTGTTTTGAACTTTATTGTTTTGTTAT
TTAAGTTTATGTTATTTATAAAAAAAAAACCTTAATAAGCTGTATCTG
TTTCATATGCTTTTAATTTTAAAGGAATAACAAAACTGTCTGGCTCAA
CGGCAAGTTTCCCTCCCTTTTCTGACTGACACTAAGTCTAGCACACAG
CACTTGGGCCAGCAAATCCTGGAAGGCAGACAAAAATAAGAGCCTGAA
GCAATGCTTACAATAGATGTCTCACACAGAACAATACAAATATGTAAA
AAATCTTTCACCACATATTCTTGCCAATTAATTGGATCATATAAGTAA
AATCATTACAAATATAAGTATTTACAGGATTTTAAAGTTAGAATATAT
TTGAATGCATGGGTAGAAAATATCATATTTTAAAACTATGTATATTTA
AATTTAGTAATTTTCTAATCTCTAGAAATCTCTGCTGTTCAAAAGGTG
GCAGCACTGAAAGTTGTTTTCCTGTTAGATGGCAAGAGCACAATGCCC
AAAATAGAAGATGCAGTTAAGAATAAGGGGCCCTGAATGTCATGAAGG
CTTGAGGTCAGCCTACAGATAACAGGATTATTACAAGGATGAATTTCC
ACTTCAAAAGTCTTTCATTGGCAGATCTTGGTAGCACTTTATATGTTC
ACCAATGGGAGGTCAATATTTATCTAATTTAAAAGGTATGCTAACCAC
TGTGGTTTTAATTTCAAAATATTTGTCATTCAAGTCCCTTTACATAAA
TAGTATTTGGTAATACATTTATAGATGAGAGTTATATGAAAAGGCTAG
GTCAACAAAAACAATAGATTCATTTAATTTTCCTGTGGTTGACCTATA
CGACCAGGATGTAGAAAACTAGAAAGAACTGCCCTTCCTCAGATATAC
TCTTGGGAGAGAGCATGAATGGTATTCTGAACTATCACCTGATTCAAG
GACTTTGCTAGCTAGGTTTTGAGGTCAGGCTTCAGTAACTGTAGTCTT
GTGAGCATATTGAGGGCAGAGGAGGACTTAGTTTTTCATATGTGTTTC
CTTAGTGCCTAGCAGACTATCTGTTCATAATCAGTTTTCAGTGTGAAT
TCACTGAATGTTTATAGACAAAAGAAAATACACACTAAAACTAATCTT
CATTTTAAAAGGGTAAAACATGACTATACAGAAATTTAAATAGAAATA
GTGTATATACATATAAAATACAAGCTATGTTAGGACCAAATGCTCTTT
GTCTATGGAGTTATACTTCCATCAAATTACATAGCAATGCTGAATTAG
GCAAAACCAACATTTAGTGGTAAATCCATTCCTGGTAGTATAAGTCAC
CTAAAAAAGACTTCTAGAAATATGTACTTTAATTATTTGTTTTTCTCC
TATTTTTAAATTTATTATGCAAATTTTAGAAAATAAAATTTGCTCTAG
TTACACACCTTTAGAATTCTAGAATATTAAAACTGTAAGGGCCTCCA
TCCCTCTTACTCATTTGTAGTCTAGGAAATTGAGATTTTGATACACCT
AAGGTCACGCAGCTGGGTAGATATACAGCTGTCACAAGAGTCTAGATC
AGTTAGCACATGCTTTCTACTCTTCGATTATTAGTATTATTAGCTAAT
GGTCTTTGGCATGTTTTTGTTTTTTATTTCTGTTGAGATATAGCCTTT
ACATTTGTACACAAATGTGACTATGTCTTGGCAATGCACTTCATACAC
AATGACTAATCTATACTGTGATGATTTGACTCAAAAGGAGAAAAGAAA
TTATGTAGTTTTCAATTCTGATTCCTATTCACCTTTTGTTTATGAATG
GAAAGCTTTGTGCAAAATATACATATAAGCAGAGTAAGCCTTTTAAAA
ATGTTCTTTGAAAGATAAAATTAAATACATGAGTTTCTAACAATTAGA
```

GenBank amino acid sequence: CAG46799.1 (SEQ ID No. 2):

```
MHKWILTWILPTLLYRSCFHIICLVGTISLACNDMTPEQMATNVNCSS
PERHTRSYDYMEGGDIRVRRLFCRTQWYLRIDKRGKVKGTQEMKNNYN
IMEIRTVAVGIVAIKGVESEFYLAMNKEGKLYAKKECNEDCNFKELIL
ENHYNTYASAKWTHNGGEMFVALNQKGIPVRGKKTKKEQKTAHFLPMA
IT
``` or human recombinant KGF (SwissProt amino acid sequence: P21781 # (SEQ ID No. 3):

```
MHKWILTWILPTLLYRSCFHIICLVGTISLACNDMTPEQMATNVNCSS
PERHTRSYDYMEGGDIRVRRLFCRTQWYLRIDKRGKVKGTQEMKNNYN
IMEIRTVAVGIVAIKGVESEFYLAMNKEGKLYAKKECNEDCNFKELIL
ENHYNTYASAKWTHNGGEMFVALNQKGIPVRGKKTKKEQKTAHFLPMA
IT
``` the human recombinant KGF palifermin (DrugBank: DB00039 (fragmented from aa. 56 to aa. 194 of SEQ ID No. 3):

```
YDYMEGGDIRVRRLFCRTQWYLRIDKRGKVKGTQEMKNNYNIMEIRTV

AVGIVAIKGVESEFYLAMNKEGKLYAKKECNEDCNFKELILENHYNTY

ASAKWTHNGGEMFVALNQKGIPVRGKKTKKEQKTAHFLPMAIT
``` or their allelic or orthologous variants, fragments, mutants, derivatives or functional analogues.

In the present invention, variants, fragments, mutants derivatives or functional analogues possess the same pharmacological activity as the KGF protein.

Preferably the KGF variant or orthologs, derivatives and fragments thereof has at least one residue replaced by a different amino acid residue.

The KGF variants of the present invention, obtained by technologies known in the art, are mutant proteins, which differ from the amino acid sequence of the wild type KGF by the mutation of one or more single amino acid. In a very preferred embodiment of the present invention, only one amino acid replacement occurs on the sequence of the native protein. It is, however, encompassed by the subject of the present invention that the native protein can be further optimised by replacement of a plurality, e.g two or more, of amino acid replacements. The variants can therefore differ from the wild type protein sequence by amino acid replacements on 1-10, preferably 1, 2, 3, 4, 5 and 6 different amino acid target positions.

Moreover, the mutants or variants of the invention exhibit the same pharmacological activity as the wild type KGF protein.

The term "mutation" or "variant" as used in the context of the present invention can be understood as substitution, deletion and/or addition of single amino acid in the target sequence. Preferably, the mutation of the target sequence in the present invention is a substitution. The substitution can occur with different genetically encoded amino acid or by non-genetically encoded amino acids. Examples for non-genetically encoded amino acids are homocystein, hydroxyproline, ornithin, hydroxylysine, citrulline, carnitine, etc.

In a preferred embodiment of the invention, the surgical intervention comprises the removal of cancer of the endometrium, including cancer of the pelvis, or para-aortic lymphadenectomy.

In a preferred embodiment, the treatment comprises adjuvant vaginal brachytherapy.

In a preferred embodiment, the chemotherapeutic agent is tamoxifen or an anti-tumoral drug belonging to the family of selective oestrogen receptor modulators.

The invention further relates to a pharmacological composition comprising pharmaceutically acceptable excipients (or carriers) and a compound for use in the treatment of conditions of vaginal atrophy, dysuria, vaginal pain and/or vaginal drying induced by a post-menopausal status, by a surgery, by a pathology and/or chemotherapy or radiotherapy treatments wherein said compound is selected from the group consisting of:
- the keratinocyte growth factor (KGF/FGF7), orthologs, derivatives and fragments thereof;
- a polynucleotide coding for said keratinocyte growth factor (KGF/FGF7) or orthologs, derivatives and fragments thereof;
- a vector comprising said polynucleotide and
- a host cell genetically engineered expressing said polypeptide.

Said pharmacological composition is preferably intended for topical administration.

The pharmacological composition according to the invention preferably comprises a pharmaceutically effective amount of keratinocyte growth factor.

In a preferred embodiment, the keratinocyte growth factor is at a concentration from 0.1 to 100 µg/ml, more preferably at a concentration of 0.1 to 10 µg/ml, still preferably 5 µg/ml. The pharmacological composition of the invention preferably also comprises a gelling agent. Said gelling agent is preferably Pluronic F127.

The pharmacological compositions of the invention can be prepared by mixing the keratinocyte growth factor having the desired degree of purity with optional vectors, excipients or physiologically acceptable stabilisers (Remington Pharmaceutical Sciences 16a edition, Osol, A. Ed., 1980) in the form of lyophilised formulations or aqueous solutions. Vectors, excipients or acceptable stabilisers are atoxic to the recipients at the doses and concentrations used and may include buffers, antioxidants, preservatives, peptides, proteins, hydrophilic polymers, chelating agents such as EDTA, sugars, salts forming counter ions such as sodium, metal complexes (for example Zn-protein complexes) and/or tested non-ionic surfactants such as TWEEN®, Pluronics® or polyethylene glycols (PEG).

Topical treatment with KGF is highly directed and specific to the local treatment of menopausal disorders and is therefore indicated in order to combat symptoms such as vaginal dryness and atrophy. KGF may therefore substitute the therapies already in use, such as formulations based on oestrogens.

The advantages provided by the use of KGF, as a result of its protein origin, are due to the impenetrability of the epithelial barrier and the physiological presence of its specific receptor in membrane, which allows to develop its function without passing through. In fact, by contrast with oestrogens, KGF does not passed into circulation (transcutaneous).

In a preferred embodiment of the pharmacological composition of the invention, KGF is administered in a dose of 10-30 ng/day, thus ensuring that only the proportion introduced and released can act locally, without cross-reacting with other signalling pathways.

The pharmaceutical composition of the present invention may be used for diagnostic or for therapeutic applications.

The exact formulation, route of administration and dosage can be chosen by the individual physician in view of the patient's conditions. Administration may be achieved in a single dose or repeated doses at intervals. Dosage amount and interval may be adjusted individually in order to provide the therapeutic effect, which results in amelioration of symptoms or a prolongation of the survival in a patient. The actual amount of composition administered will, of course, be dependent on the subject being treated, on the subject's weight, the severity of the affliction, the manner of administration and the judgement of the prescribing physician. A suitable daily dosage will be between 0.001 to 10 mg/kg, particularly 0.1 to 5 mg/kg. The administration may be carried out by known methods, e.g. by injection, in particular by intravenous, intramuscular, transmucosal, subcutaneous or intraperitoneal injection and/or by oral, topical, nasal, inhalation, aerosol and/or rectal application, etc. The administration may be local or systemic. In addition, the HMGB1 variants object of this invention can be reversibly immobilized and/or adsorbed on the surface and/or inside medical devices or drug release/vehicling systems (microspheres). Medical devices and microspheres can be reversibly loaded with the variants of this invention, through their binding, impregnation and/or adsorption on the surface of the medical device or of the microsphere or on a layer that coats its surface. When the medical device or the microsphere come into contact with biological fluids, the reversibly immobilized variant is released. Therefore, the medical device and the microsphere act as drug-releasing tools that elute the molecule object of this invention in such a way that their release kinetics can be controlled, ensuring controlled or sustained release, as required by the treatment. The methods for coating/impregnating the medical devices and loading microspheres are well known by experts in these technologies.

In the present invention a polypeptide comprising an amino acid sequence having at least 70% identity with the sequence of SEQ ID No. 1 is another embodiment. Said polypeptide is chosen from the group consisting of a homologue, a derivative, an equivalent, and a fragment of a polypeptide.

As used herein, the term "equivalent" will be understood to mean a peptide having at least one of the activities of the instant polypeptide. "Homologue" will be understood as a polypeptide exhibiting certain modifications compared with the natural polypeptide. These modifications can be a deletion, a truncation, an extension, a chimeric fusion, and/or a mutation. Among equivalent polypeptides, those who display more than 80% homology are preferred.

"Derivative" refers to any polypeptides, eventually mutated, truncated, and/or extended, which have been chemically modified or contain unusual amino acids.

As used herein, the term "polypeptide" refers to a molecular chain of amino acids having therapeutic properties to treat conditions of vaginal atrophy, dysuria, vaginal pain and/or vaginal drying induced by a post-menopausal status, by a surgery, by a pathology and/or chemotherapy or radiotherapy treatments. This polypeptide, if required, can be modified in vitro and/or in vivo, for example by glycosylation, myristoylation, amidation, carboxylation or phosphorylation, and may be obtained, for example, by synthetic or recombinant techniques known in the art.

As used herein, the term "orthologs" refers to proteins in different species than the proteins SEQ ID NO.1 in *Homo sapiens* that evolved from a common ancestral gene by speciation. As an example of such orthologs, one can cite the proteins corresponding to KGF in *Mus musculus, Rattus norvegicus Gallus gallus, Xenopus laevis* and *Danio rerio*.

As used herein, the term "derivatives" refers to polypeptides having a percentage of identity of at least 75% with SEQ ID NO. 1, or ortholog thereof, preferably of at least 85%, as an example of at least 90%, and more preferably of at least 95%.

As used herein "fragments" refers to polypeptides having a length of at least 25 amino acids, preferably at least 50 amino acids, as an example at least 75 or 85 amino acids, and more preferably of at least 100 amino acids. In the present invention all fragments and derivatives possess therapeutic properties to treat conditions of vaginal atrophy, dysuria, vaginal pain and/or vaginal drying induced by a post-menopausal status, by a surgery, by a pathology and/or chemotherapy or radiotherapy treatments.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest.

Sequences comparison between two amino acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p: 482, 1981), by using the local homology algorithm developed by NEDDLEMAN and WUNSCH (J. Mol. Biol, vol. 48, p: 443, 1970), by using the method of similarities developed by PEARSON and LIPMAN (Proc. Natl. Acd. Sci. USA, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C, Nucleic Acids Research, vol. 32, p: 1792, 2004). To get the best local alignment, one can preferably used BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "excipient or carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein, the term "polynucleotide" refers to RNA or DNA, preferably to DNA. Said DNA may be double-stranded or single-stranded.

Preferably, the polynucleotide comprises the sequence of SEQ ID No. 1. Preferably, the polynucleotide comprises a sequence which encodes the sequence of KGF (SEQ ID No. 2, or SEQ ID No. 3 or from aa 56 to aa 194 of SEQ ID No. 3).

The polynucleotide of the invention may also include the coding sequence of the polypeptide defined previously, additional coding sequence such as leader sequence or a proprotein sequence, and/or additional non-coding sequence, such as introns or 5 'and/or 3' UTR sequences.

As used herein, the term "vector" refers to an expression vector, and may be for example in the form of a plasmid, a viral particle, a phage, etc. Such vectors may include bacterial plasmids, phage DNA, baculovirus, yeast plasmids, vectors derived from combinations of plasmids and phage DNA, viral DNA such as vaccinia, adenovirus, fowl pox virus, and pseudorabies. Large numbers of suitable vectors are known to those of skill in the art and are commercially available. The following vectors are provided by way of example. Bacterial: pQE70, pQE60, pQE-9 (QIAGEN), pbs, pDIO, phagescript, psiX174, pbluescript SK, pbsks, pNH8A, pNH1[beta]a, pNH18A, pNH46A (STRATAGENE), ptrc99a, pKK223-3, pKK233-3, pDR540, pRIT5 (PHARMACIA). Eukaryotic: pWLNEO, pSV2CAT, pOG44, pXT1, pSG (STRATAGENE), pSVK3, pBPV, pMSG, pSVL (PHARMACIA). However, any other vector may be used as long as it is replicable and viable in the host. The polynucleotide sequence, preferably the DNA sequence in the vector is operatively linked to an appropriate expression control sequence(s) (promoter) to direct mRNA synthesis. As representative examples of such promoters, one can mentioned prokaryotic or eukaryotic promoters such as CMV immediate early, HSV thymidine kinase, early and late SV40, LTRs from retrovirus, and mouse metallothionein-I. The expression vector also contains a ribosome binding site for translation initiation and a transcription vector. The vector may also include appropriate sequences for amplifying expression.

In addition, the vectors preferably contain one or more selectable marker genes to provide a phenotypic trait for selection of transformed host cells such as dihydro folate reductase or neomycin resistance for eukaryotic cell culture, or such as tetracycline or ampicillin resistance in *E. coli*.

As used herein, the term "host cell genetically engineered" relates to host cells which have been transduced, transformed or transfected with the polynucleotide or with the vector described previously.

As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein.

Preferably, said host cell is an animal cell, and most preferably a human cell.

The introduction of the polynucleotide or of the vector described previously into the host cell can be effected by method well known from one of skill in the art such as calcium phosphate transfection, DEAE-Dextran mediated transfection, or electroporation.

The composition of the invention may comprise one or more additives (e.g., stabilizers, preservatives). See, generally, Ullmann's Encyclopedia of Industrial Chemistry, 6th Ed. (various editors, 1989-1998, Marcel Dekker).

According to the present invention, an "effective amount" of a composition is one which is sufficient to achieve a desired biological effect, in this case, the treatment of conditions of vaginal atrophy, dysuria, vaginal pain and/or vaginal drying induced by a post-menopausal status, by a surgery, by a pathology and/or chemotherapy or radiotherapy treatments. It is understood that the effective dosage will be dependent upon the age, sex, health, and weight of the recipient, kind of concurrent treatment, if any, frequency of treatment, and the nature of the effect desired. The ranges of effective doses provided are not intended to limit the invention and represent preferred dose ranges. However, the preferred dosage can be tailored to the individual subject, as is understood and determinable by one of skill in the art, without undue experimentation. Said polypeptide, polynucleotide, vector, and host cell are as described previously.

BRIEF DESCRIPTION OF THE DRAWINGS

The present invention will be described by non-limiting examples with reference to the following figures:

FIG. 1. Effect of the treatment with KGF and E2 on the proliferation of KC. (A) immunofluorescence analyses with a direct polyclonal antibody against Ki67 in untreated or treated KC with different concentrations of KGF or E2 (0.5-20 ng/ml) for 24 h. (B) Assessment of the proliferation of the cells after treatment with KGF and E2 (20 ng/ml) in two different populations of KC, derived from biopsies taken from pre-menopausal or post-menopausal women respectively. (C) Assessment of the possible synergistic or additive effect of KGF and E2. KC cells were treated with KGF, E2 or a combination thereof and subjected to immunofluorescence with anti-Ki67 antibody. (D) Assessment of the proliferative effect of KGF and E2 in the presence of tamoxifen. KCs were treated with KGF, E2, tamoxifen (Tam, 100 nM), KGF then Tam or E2 then Tam for 24 h. After 24 h, the cells were fixed and stained with crystal violet 1% or subjected to immunofluorescence with anti-Ki67 antibody. The percentage of positive cells for Ki67 was determined by counting the number of Ki67-positive nuclei compared to the total number of nuclei in ten different areas selected at random from three different experiments. The error bars represent the standard deviation.

FIG. 6. Studies in vivo on a mouse model. (A) The strain of mouse CD1 used in this study was subjected to ovariectomy in order to induce vaginal atrophy and was therefore treated locally with 25 μl of hydrogel loaded with KGF (10 or 30 ng/day) or with E2 (30 ng/day or 1 ug/day). (B) Rheological study on hydrogel of Pluronic F127. A solution of F127 (cP=20% w/v in $H_2O$) was heated at a rate of 2° C./min from 10 to 40° C., and the G' values (modulus of elasticity) and G" (modulus of loss) were measured during this rise in temperature and were recorded in the form of a graph. (C) Schematic diagram of the model molecules used for the in vitro release test with Pluronic F127. (D) Release test with Pluronic F127. Hydrogel loaded with the model molecules was introduced into a dialysis membrane bag and incubated in 60 ml of distilled water at 37° C. under stirring at a rate of 50 rpm. The release profiles of the loaded hydrogels were expressed in cumulative output percentages over time.

FIG. 8. Quantification of the in vivo effect of KGF and E2 on vaginal epithelium. (A) The sections of tissue from the vagina of control mice, mice subject to ovariectomy and treated with the vehicle only, and mice treated with low and high doses of E2 or KGF were stained with hematoxylin and eosin. Cornificated vaginal epithelium was observed in the vagina exposed both to E2 and to KGF, but not in the group treated with the vehicle (40× enlargement compared to the original). (B) The number of epithelial layers, the thickness of the epithelium and the ratio between the epithelial surface and the length of the basal membrane were calculated for each treatment. In short, three animals per each group were treated and three images were captured for each animal. Average values were obtained from five measurements of each image. The vertical bars represent the standard errors.

DETAILED DESCRIPTION OF THE INVENTION

Examples

Figure 2:
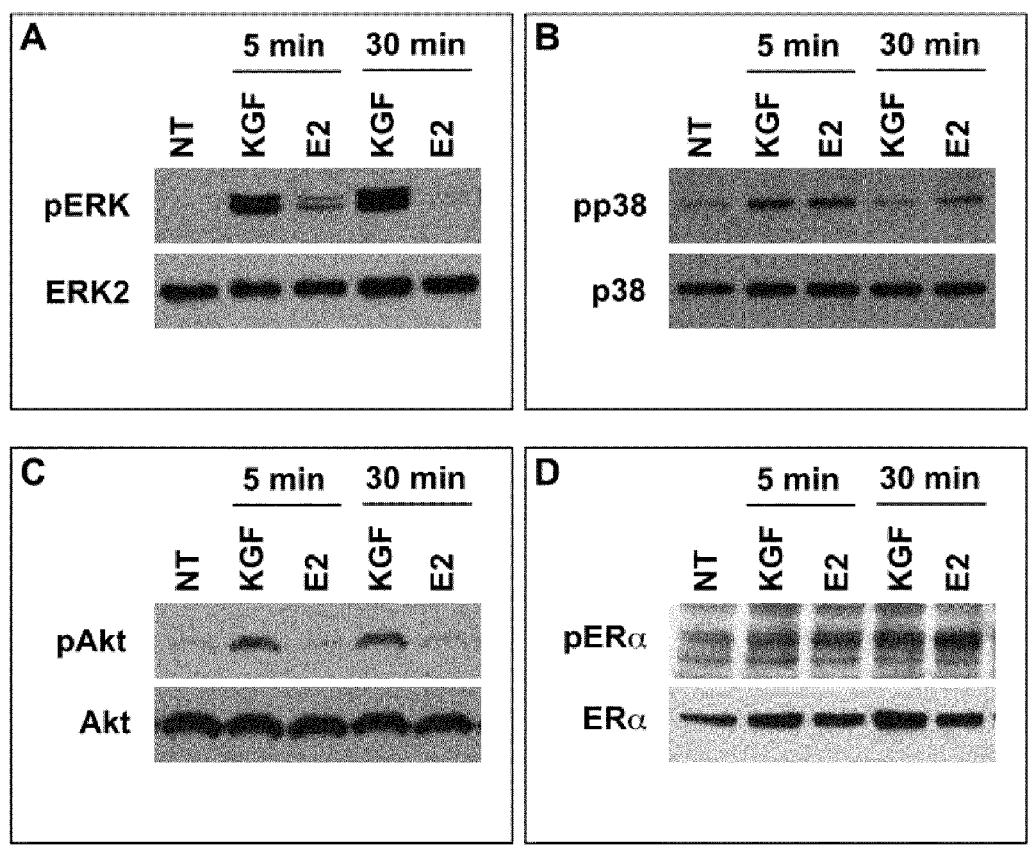
FIG. 2. Effect of KGF and E2 on the activation of the non-genomic pathways of ER-alpha. (A) MCF-7 cells were treated with KGF and E2 (20 ng/ml) for 5 or 30 minutes, and Western blot analysis of the phosphorylation state of ERK was carried out using a phosphospecific monoclonal ERK antibody (pERK). The levels of total ERK were assessed by "blotting" with an ERK2-specific antibody. (B) Western blot analysis of the phosphorylation state of MAPK p38 was carried out using a phosphospecific monoclonal p38 antibody (pp38). The levels of total p38 were assessed by "blotting" with a p38-specific antibody. (C) Western blot analysis of the state of phosphorylation of Akt was carried out using a phosphospecific monoclonal Akt antibody (pAkt). The levels of total Akt were assessed by "blotting" with an Akt-specific antibody. (D) Western blot analysis of the phosphorylation state of ERalpha was carried out using a phosphospecific monoclonal ERalpha antibody (pERa). The levels of total ERalpha were assessed by "blotting" with an ERα-specific antibody.

Materials and Methods
Cell Cultures and Treatments

The oestrogen receptor α-positive MCF-7 human breast adenocarcinoma cell line, acquired from American Type Culture Collection (no. HTB-22, ATCC-LGC Promochem, Teddington, UK), was cultured in Dulbecco's modified eagle's medium (DMEM; Invitrogen, Karlsruhe, Germany), supplemented with 10% foetal bovine serum (FBS; Invitrogen) and antibiotics. Primary cultures of human oestrogen-sensitive keratinocytes (KCs) were established from 1 $cm^2$ full-thickness mucosal biopsy of the vaginal vestibule. Following enzymatic dissociation, the keratinocytes were seeded onto culture plates coated with collagen IV (10 mg/ml), as previously reported [Panici et al, 2007], and were maintained in basal medium of the keratinocytes (KBM, Lonza) supplemented with aliquots of KGM (Lonza), with medium change twice a week. For all the experiments with 17β-oestradiol (E2) and tamoxifen, the MCF-7 cells were cultivated in DMEM without phenol red with 10% FBS treated with dextran/carbon (Invitrogen), and the KCs were transferred to a steroid medium of reduced concentration (KGM without EGF and BPE). Both MCF-7 and KC were deprived of serum for 4 hours and then treated for 48 h with human recombinant KGF (Upstate Biotechnology, Lake Placid, N.Y.), E2 (Sigma-Aldrich, Milan, Italy), tamoxifen (Sigma-Aldrich, 100 nM) or combinations thereof.

Quantitative RT-PCR

The cells were harvested and the total RNA was extracted with the use of TRIzol reagent (Invitrogen). cDNA was generated with oligo (dT) from 1 μg of RNA using the SuperScript III reverse transcriptase kit (Invitrogen). After reverse transcription, the abundance of KGFR in MCF-7 cells treated and untreated with E2 was quantified by Q-RT-PCR. For KGFR, specific personalised TaqMan® assays were developed (Applied Biosystems of Life Technologies, Carlsbad, Calif., USA) (KGFR "forward", 5'-GGCTCTGT-TCAATGTGACCGA-3' SEQ ID NO. 4; KGFR "reverse", 5'-GTTGGCCTGCCCTATATAATTGGA-3' SEQ ID NO. 5. TaqMan probe, 5'-TTCCCCAGCATCCGCC-3' SEQ ID NO. 6), used as a concentration of 1× per well. A total of 2 μl/plate well was added to the sample wells along with Taqman Universal PCR master mix at a concentration of 1× and water to a volume of 25 μl/well. The assays were conducted in triplicate on an ABI 7500 Real Time instrument (Applied Biosystems) using the following conditions: 50° C. for 2 min, 95° C. for 10 min, and then 95° C. for 15 s and 60° C. for 1 min, repeated 40 times. Relative quantification was performed using mRNA 18s as an endogenous control. The data were expressed as a rise of mRNA of KGFR compared to the control.

Immunofluorescence Microscopy

The cells, grown on glass coverslips, were treated as described above, then fixed in 4% paraformaldehyde in phosphate-buffered saline (PBS) for 30 min at 25° C., followed by treatment with 0.1 M glycine in PBS for 20 min at 25° C. and with 0.1% Triton X-100 in PBS for an additional 5 min at 25° C. to allow permeabilisation. To assess cell proliferation, the cells were incubated with an anti-Ki67 rabbit polyclonal antibody (1:50 in PBS; Zymed Laboratories, San Francisco, Calif.), which identifies cycling cells. The primary antibody was visualised using Texas Red conjugated goat anti-rabbit IgG (1:100 in PBS; Jackson ImmunoResearch Laboratories, West Grove, Pa.). The nuclei were visualised using 4',6-diamido-2-phenylindole dihydrochloride (DAPI) (1:10000 in PBS; Sigma-Aldrich). Fluorescence signals were analysed by recording stained images using a cooled CCD colour digital camera SPOT-2 (Diagnostic Instruments Incorporated, Sterling Heights, Mich.) and Axiovision software (Carl Zeiss Inc., Oberkochen, Germany).

The percentage of Ki67-positive cells was evaluated by counting, for each treatment, a total of 500 cells, randomly taken from ten microscopic fields in three different experiments, expressed as mean value±95% CI and recorded as graphs. For the experiments concerning localisation of ERα, the cytoskeleton of actin was visualised using TRITC phalloidin (1:100 in PBS) and ERα was visualised using an anti-ERα monoclonal antibody (Santa Cruz) (1:100 in PBS). The stained single and combined images were captured using Zeiss Apotome® and AxioVision software (Carl Zeiss, Jena, Germany) using 40× lenses.

Cell Survival Assay

To evaluate the cytotoxicity of cells treated with tamoxifen, the MCF-7 cells were treated as described above, fixed for 10 min in a solution of 10% acetic acid-10% methanol, stained with crystal violet (1% w/v) and photographed using a Power Shot G5 digital camera (Canon, Inc., Tokyo, Japan).

Western Blot Analyses

MCF-7 cells untreated or treated with KGF or E2 were lysed in RIPA buffer. Total proteins (50-150 µg) were broken down under reducing conditions by 7%-10% SDS-PAGE and transferred to Immobilon-FL membranes (Millipore, Billerica, Mass.). The membranes were blocked in TBS containing 0.5% Tween 20 (TBS-T) and 5% milk for 1 hour at 25° C. and were then washed twice for 20 minutes in each case in TBS-T. The membranes were incubated overnight at 4° C. with the primary antibody. The primary antibodies used were as follows: antiphospho-p44/42 MAPK, antiphospho-Akt, anti-Akt, antiphospho-p38, anti-p38, antiphospho-ERα (Cell Signaling Technology, Inc., Danvers, Mass., USA), anti ERK2, anti-Bek (C-17), anti-ERα, anti-lamin B (Santa Cruz Biotechnology, Santa Cruz, Calif., USA), anti-tubulin (Sigma-Aldrich). The membranes were then incubated with secondary antibody conjugated with horseradish peroxidase (HRP) (Sigma-Aldrich) for 1 hour at 25° C. The bound antibody was detected by enhanced chemiluminescence detection reagents (Pierce Biotechnology, Inc, Rockford, Ill., USA), according to manufacturer's instructions. The tubulin was controlled so as to normalize. Densitometric analysis was performed using Quantity One Program (Bio-Rad Laboratories srl, Segrate, MI, Italy).

Sub-Cellular Fractionation

The cells were harvested in PBS and centrifuged at 2000 rpm for 5 minutes to obtain a pellet, resuspended in cellular lysis buffer containing Hepes 10 mM pH 8, 50 mM NaCl, 1 mM EDTA pH 8, 0.2% TritonX100, sucrose 500 mM and protease inhibitors, stirred, and placed in ice for 15 min. After centrifugation at 13000 rpm for 10 min at 4° C., the supernatant represented the cytoplasmic fraction. The pellet was then washed twice with a nuclei washing buffer containing Hepes 10 mM pH 8, 50 mM NaCl, 0.1 mM EDTA pH 8 and 25% glycerol. The nuclear protein fraction was obtained after centrifugation at 13000 rpm for 10 min at 4° C. and incubation of the pellet for 15 min at 4° C. with a buffer containing Hepes 10 mM pH 8, 350 mM NaCl, 0.1 mM EDTA pH 8 and 25% glycerol. The efficiency of the fractionation was analysed by means of immunoblotting using an anti-β-tubulin antibody as cytoplasmic marker and an anti-lamin B antibody as nuclear marker.

Cellular Transfection and Dual-Luciferase Reporter Assay

MCF-7 cells were seeded onto 24-well plates with a cell/well density of $2 \times 15^5$ and were co-transfected with 1 µg of the 3×ERE TATA LUC construct, a plasmid containing the reporter gene for firefly luciferase under the control of three DNA sequences to which the ER binds, called oestrogen response elements (EREs) (Addgene), and with 300 ng of control pRL-TK plasmid (renilla luciferase) for normalisation of the efficiency of the transfection process. The transfections were carried out using lipofectamine 2000 (Invitrogen) according to manufacturer's instructions. After 6 h, the cells were treated with KGF or E2. The luciferase activity was determined using a dual-luciferase reporter assay system (Promega) 24 h after the treatment, according to manufacturer's protocol. All the transfections were conducted in triplicate.

Rheological Studies of Pluronic F127

Pluronic F127 ($PEO_{100}$-$PPO_{65}$-$PEO_{100}$) (PM≈12600) (cat. P2443, Sigma Aldrich, Milan, Italy), an amphiphilic synthetic polymer formed from polyethylene oxide and polypropylene oxide, when dissolved in water at high concentrations (>15%), has the characteristic of becoming liquid at temperatures less than 25° C. and acquires the consistency of a hydrogel at higher temperatures. To demonstrate the solution-gel transition that occurs with the increase in temperature, a rheological study of a solution of F127 (cP=20% w/v in $H_2O$) was carried out, heating the solution at a rate of 1° C./min from 10 to 40° C. and measuring, during this rise in temperature, the G' value (modulus of elasticity) and the G" value (modulus of loss): these parameters describe, respectively, the ability to accumulate and dissipate energy and describe the resilient or viscous nature of a material. Specifically, a substance in the liquid state is characterised by G" values greater than G' values, and, vice versa, a substance in gel form has G" values lower than G' values.

In Vitro Release Test of Pluronic F127

For the in vitro release test, two model molecules were used: myoglobin, a hydrophilic protein of PM comparable to KGF, and prednisolone, a lipophilic hormone characterised by a chemical structure similar to that of E2. 2 mL of loaded hydrogel containing 4 mg of myoglobin or prednisolone in a solution of 20% Pluronic F127 w/v were introduced into a dialysis membrane bag (MWCO 3500 Da), and the dialysis bag sealed at the end was incubated in 60 mL of release medium (distilled water) at 37° C. and was stirred at a rate of 50 rpm. Saturation conditions were avoided by means of frequent substitution of fresh water. At predetermined intervals, aliquots of 0.5 mL of release medium were removed and substituted with an equal volume of fresh solution. The release behaviour in vitro of hydrogel loaded with myoglobin was compared with that of hydrogel loaded with prednisolone. All the assays were conducted in triplicate. Release profiles were expressed in cumulative release percentages over time.

Animals

The mouse strain CD1 was used in this study (Charles Rivers). The mice were held in a standard housing for laboratory animals with controlled lighting (12 h/day) and temperature (25±1° C.) and were provided with food and water ab libitum. All the experimental protocols concerning animals were in line with the Guidelines of Sapienza University for the care and use of laboratory animals and were approved by the Ethical Committee of the aforesaid institution. Forty female mice were subjected to an ovariectomy for the purpose of inducing vaginal atrophy and were administered a diet of Altromin C1000 without phytoestrogens (Altromin, Lage, Germany) for the duration of the experiments. After 30 days, the mice were treated locally, introducing daily into the vaginal canal 25 µl of hydrogel loaded with KGF (10 or 30 ng/day) or with E2 (30 ng/day or 1 µg/day). A control group was treated only with hydrogel. After 60 days of treatment, the mice were killed and the vaginas were immediately explanted, fixed in formalin and processed for histological analysis.

Histology

Serial sections of the vaginal mucus obtained from four groups of mice were stained with hematoxylin/eosin, placed permanently under a glass plate and analysed histologically. The thickness and the strata of epithelial cells of the vagina were then determined in three animals for each group, in three images for each animal (10× enlargement). Mean values were obtained from five measurements of each image. For the purpose of quantifying the thickness of the vaginal epithelium, the vertical distance between the lower surface of the cells in the stratum basale and the apical surface of the cells in the stratum superficiale was measured with the aid of NIH Image J v 1.56 (National Institutes of Health, Bethesda, Md.), and denoted as thickness. To estimate the number of vaginal epithelial layers, the layer of cells covering five contiguous basal cells was counted in the sample.

Immunohistochemistry

Serial sections of the vaginal mucus obtained from the four groups of mice were analysed for the expression of PCNA (Proliferating Cell Nuclear Antigen, a marker of cell proliferation) by means of immunohistochemistry. The sections were elaborated using the technique of avidin-biotin-peroxidase complex (DAKO, Glostrup, Denmark) and incubated with mouse anti-A-rat-PCNA monoclonal antibody (clone P10, 1:4000) (Abcam, Cambridge, UK), which recognises proliferant cells.

Enzyme-Linked Immunosorbent Assay (ELISA)

The concentrations of E2 and KGF in the serum of treated mice were measured using an ELISA standard kit (R & D Systems, Minneapolis, Minn., USA). The sensitivity of the ELISA assay was ≥10 pg/mL. Standard preparations of E2 or KGF were used as internal controls. The values are presented as mean±standard deviation.

Statistical Analysis

Each series of experiments was repeated at least in triplicate, and the standard deviation values were calculated. The student's t-test was used for the statistical analysis, and the p-values less than 0.05 were considered statistically significant.

Results

Comparison of the Efficacy of KGF and E2 in Induction of In Vitro Proliferation of the Vaginal Epithelium For the purpose of verifying the possibility of using KGF as an alternative therapeutic medium compared to administration of oestrogens, the authors first compared the effect of KGF and E2 on vaginal epithelium reconstructed in vitro from a biopsy of the vaginal vestibule. The possibility of reconstructing in vitro strips of vaginal mucus derives from the experience, now consolidated of the authors, in the reconstruction of autologous neovagina in patients suffering from Mayer Rokitansky Kuster Hauser syndrome (MRKHS) (Panici et al, 2007). For the study, 20 pre-menopausal patients and 16 post-menopausal patients were enrolled and had undergone surgery for unrelated illnesses, from whom the authors were able to sample, after informed agreement, biopsies of vaginal mucus from which primary cell cultures were obtained. For each patient, the authors subjected the culture of vaginal mucus obtained in vitro to treatment with various doses of E2, KGF or a combination of the two, with the aim of comparing their effects in terms of cell proliferation (assessed by immunofluorescence techniques), determining the percentage of cells positive for the antigen Ki67, a marker of cycling cells. The proliferative capacity of KGF and that of E2 were compared by producing a dose-response curve (FIG. 1A). The results obtained indicated a slightly greater efficacy in terms of cell proliferation of E2 (1.2 fold increase) compared to KGF, but only at low doses (0.5 ng/ml). At the doses used commonly in literature (20 ng/ml for KGF and 2.7 ng/ml for E2), the proliferative effect of KGF was absolutely comparable to that of the hormone. The data obtained from the two groups of patients (pre-menopausal and post-menopausal) were analysed separately to determine any differences in the efficacy of the treatment with E2 or KGF. In spite of a difference in the basal levels of proliferation (higher in the cells of young patients and lower in those of post-menopausal patients), the results indicate that, in both populations, KGF was able to stimulate proliferation of the vaginal epithelium in a manner comparable to that of oestradiol (FIG. 1B).

In another set of experiments, the combined effect of both factors, KGF and E2, was analysed, but no synergistic or additive effect was demonstrated (FIG. 1C).

At the same time, vaginal mucus cells of both groups were subjected to a pre-treatment with tamoxifen in order to verify the effect of this chemotherapy drug on the proliferation induced by KGF or oestrogens. The data obtained, both via immunofluorescence with anti-Ki67 and via staining of the living cells with crystal violet, demonstrated that, whilst the proliferative effect of E2 is inhibited by the presence of tamoxifen, KGF is able to stimulate cell proliferation even in the presence of tamoxifen (FIG. 1D). Such evidence suggests that KGF could be effective in the treatment of post-menopausal disorders even in oncological patients subjected to chemotherapy with tamoxifen in order to treat oestrogen-sensitive tumours, which implies in these patients an inefficacy of local treatment with oestrogens.

Analyses of the Cross-Talk Between the Transduction of the Signal Activated by E2 and KGF Indications of the existence of a cross-talk between the signalling pathway of the oestrogen receptor and that of the receptor tyrosine kinase were already obtained for EGF/EGFR and for IGF-IR. The authors have therefore analysed, in a cellular model represented by the MCF-7 breast carcinoma cell line expressing both KGFR and the oestrogen receptor ER alpha, the potential cross-talk between the signalling pathway activated by oestrogens and the signalling pathway mediated by the KGF/KGFR bond. It is known that oestrogens are regulators of growth and differentiation in a wide range of target tissues, including reproductive organs, the mammary gland, the nervous system, the cardiovascular system, and the skeletal system. These are also involved in many pathological processes, in particular breast tumours and endometrial tumours. The biological effects of oestrogens are primarily mediated by the bond and activation of ERα, ER beta and the receptor GPER. Era and ERb regulate transcription, interacting with the oestrogen response elements (EREs) localised inside the promoter of the target genes. Apart from this defined "genomic" pathway or classic pathway, there has been growing proof in recent years that the biological responses to oestrogens can be mediated by signals initiated at membrane level, which trigger a rapid intracellular transduction, activating the signalling pathway such as that of MAPK or PI3K/Akt. Such signals are indicated as "non-genomic" pathways of the ER. In particular, this pathway is responsible for the rapid effects induced by oestrogens, including the transactivation of the epidermal growth factor receptor (EGFR) and the stimulation of the transcription of the gene for IGF-IR.

To verify the level of activation of the signal pathways involved in the non-genomic pathway with regard to E2 and KGF, the authors investigated the activation of MAPK ERK1 and 2 in MCF-7 cells, in which they demonstrated the consistent and constant activation of MAPK induced by KGF after 5 and 30 minutes of treatment. By contrast, after treatment with E2, a less consistent rise in the levels of phosphorylation of ERK1 and 2 limited to 5 min of treatment was observed, whereas the activation of ERK 1 and 2 was considerably reduced with longer times (30 min, FIG. 2A). The authors therefore proceeded to analyse the activation of another non-genomic pathway of oestrogens—that of p38. In this case too, it appears that both treatments were able to phosphorylate the protein p38 (FIG. 2B). The authors then carried out experiments aimed at enhancing the activation of the PI3K/Akt pathway after treatment with KGF or E2 for the purpose of verifying whether this pathway is also activated by both factors and can therefore represent a further point of contact between the pathway of oestrogens and that of KGFR. To this end, the phosphorylation of Akt was analysed. The results obtained demonstrated similar effect of KGF and E2 in the activation of Akt (FIG. 2C). This confirms that the cross-talk between the two pathways is upstream of the activation of these three signal pathways and seems to suggest a collaboration between the two signals at the plasma membrane.

The analyses of the ligand-independent activation of the oestrogen receptor following treatment with KGF, by means of Western blot with specific antibodies able to recognise the active form of the receptor (phosphorylated in Ser118), has also demonstrated that KGF is able to induce, equally to E2, phosphorylation of ER alpha, confirming a direct role of KGF in the non-genomic pathway of oestrogens (FIG. 2D).

Figure 3:
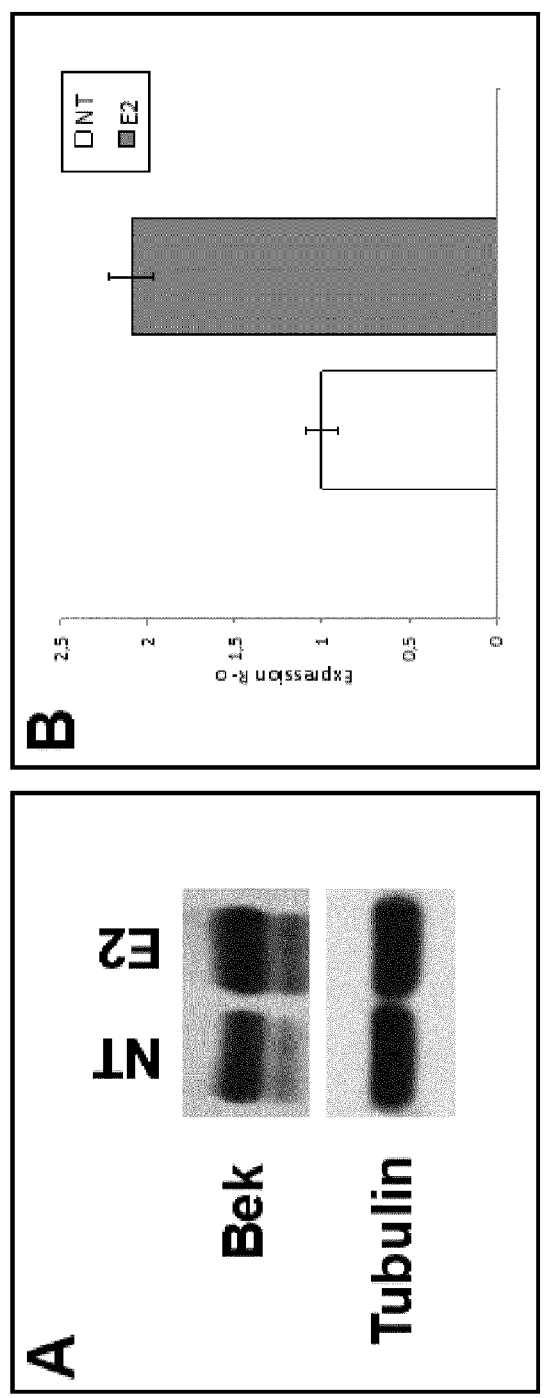
FIG. 3. Assessment of the E2-mediated upregulation of KGFR. (A) MCF-7 cells were treated or untreated with E2 (20 ng/ml) for 24 h, and the quantity of KGFR protein was assessed by means of Western blot using a polyclonal anti-bek ERK antibody. Tubulin was used as a loading control. (B) The levels of expression of mRNA of KGFR were determined using real-time PCR and normalised for the levels of mRNA 18s. The quantity of mRNA of KGFR in cells treated with E2 was expressed as an increase in the level of mRNA of KGFR compared to untreated cells.

At the same time as the study of the transduction pathway of the signal, an analysis of the levels of expression of the KGFR receptor in MCF-7 cells treated with E2 was also carried out. The results obtained by means of Western blot clearly indicate a rise in the protein KGFR determined from the treatment with E2 (FIG. 3A). The analysis of the cellular mRNA carried out by means of real time PCR also shows an over-regulation of the expression of KGFR after treatment with E2 (2.2 fold increase) (FIG. 3B), which, given the role of KGF/KGFR in the activation of the non-genomic pathway of ER, could represent an important mechanism for increasing the effect of oestrogens on the epithelial tissue.

Figure 4:
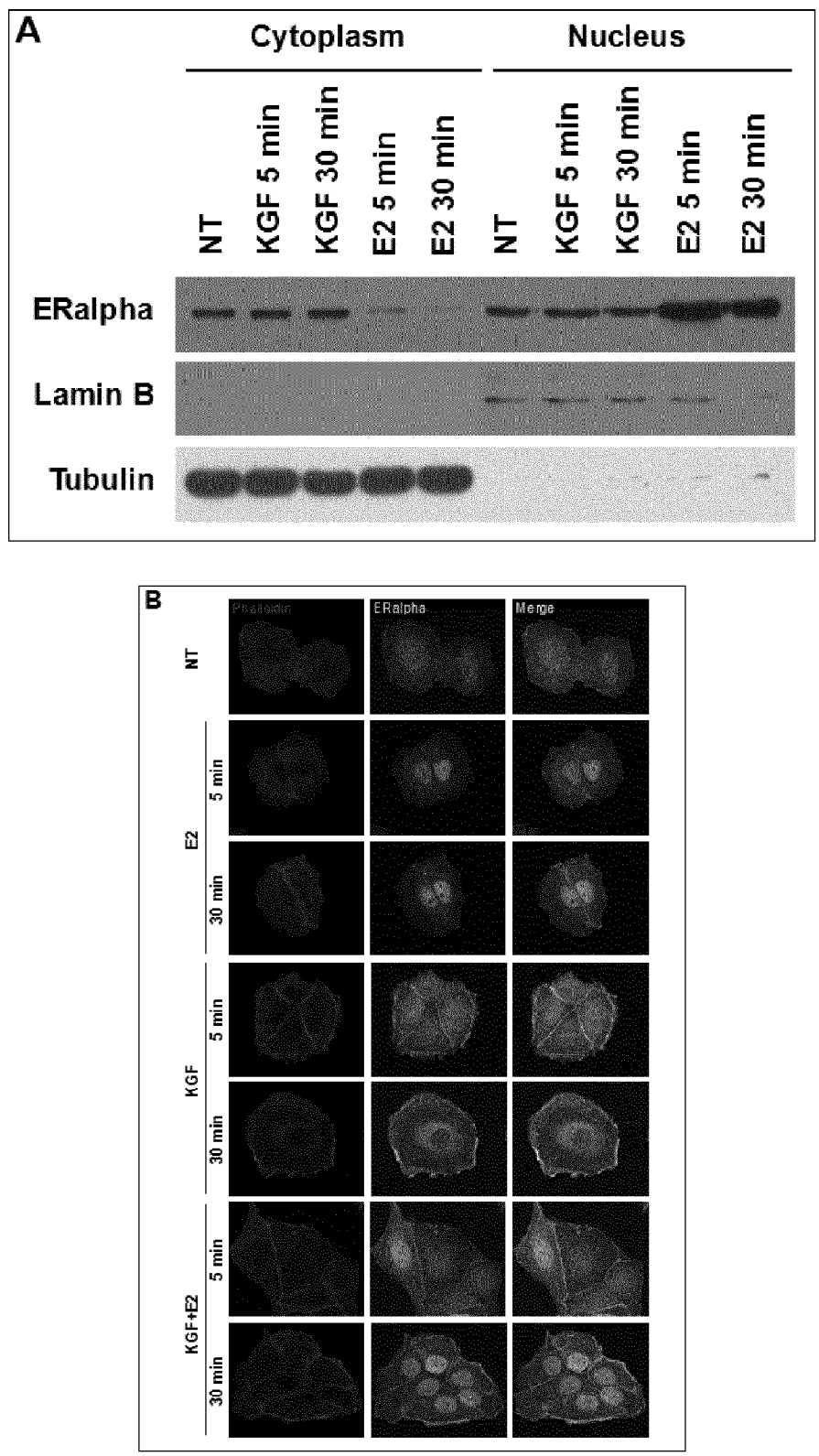
FIG. 4. Cellular localisation of ERalpha after treatment with KGF or E2. (A) Sub-cellular fractionation of MCF-7 cells. The cytoplasmic and nuclear fractions were analysed with anti-ERalpha, anti-β-tubulin as control for the cytoplasmic fractionation and anti-lamin B as nuclear marker. (B) Immuno fluorescence of MCF-7 treated or untreated with KGF, E2 or a combination thereof for 5 or 30 min. The cells were treated with primary anti-ERalpha antibodies followed by secondary antibodies conjugated with FITC (green). Microfilaments of actin were evidenced with Texas red conjugated to phalloidin (red). Merged images are shown.

The genomic pathway instead ensures that ERalpha, once activated by its ligand E2, relocates in the nucleus, where it stimulates the transcription of its target genes by means of the binding to ERE sequences. To verify whether KGF also stimulates the genomic pathway of oestrogens, the authors carried out nucleocytoplasmic fractionation experiments on lysates of MCF-7 cells treated with E2 or KGF at various times, followed by Western blot with anti-ER antibodies on both fractions. The purity of the two fractions was checked, using, as control, a protein expressed exclusively in the cytoplasm (tubulin) and a protein expressed in the nucleus (lamin B). The results demonstrated that, in the absence of treatment, ER is distributed uniformly in the two fractions, whereas after treatment with E2, even after 5 minutes, there is a dramatic redistribution of ER in the nucleus, with a considerable reduction of its quantity in the cytoplasmic fraction. Treatment with KGF instead, at the same doses and at the same times, does not appear able to induce any significant redistribution of the receptor in the nucleus (FIG. 4A). To better understand such results and verify the effective localisation of the ER after treatment with KGF, immunofluorescence experiments with a specific antibody were carried out. The analysis was carried out by means of fluorescence microscopy with the Apotome module in order to obtain optical sections and in order to identify the localisation of additional signals. In particular, the analysis, carried out by marking the cellular cytoskeleton with phalloidin-TRITC, the nucleus with DAPI and the ER with a specific antibody followed by a secondary antibody FITC, has made it possible to evidence the movement of ER in the nucleus after treatment with E2 (confirming the nucleocytoplasmic fractionation data), but also to identify an unexpected localisation of ER on the plasmatic membrane after treatment with KGF (FIG. 4B).

A direct contact between KGFR and ER at the plasmatic membrane, mediated by KGF is postulated. KGF would therefore act to drive ER toward the non-genomic pathway.

Figure 5:
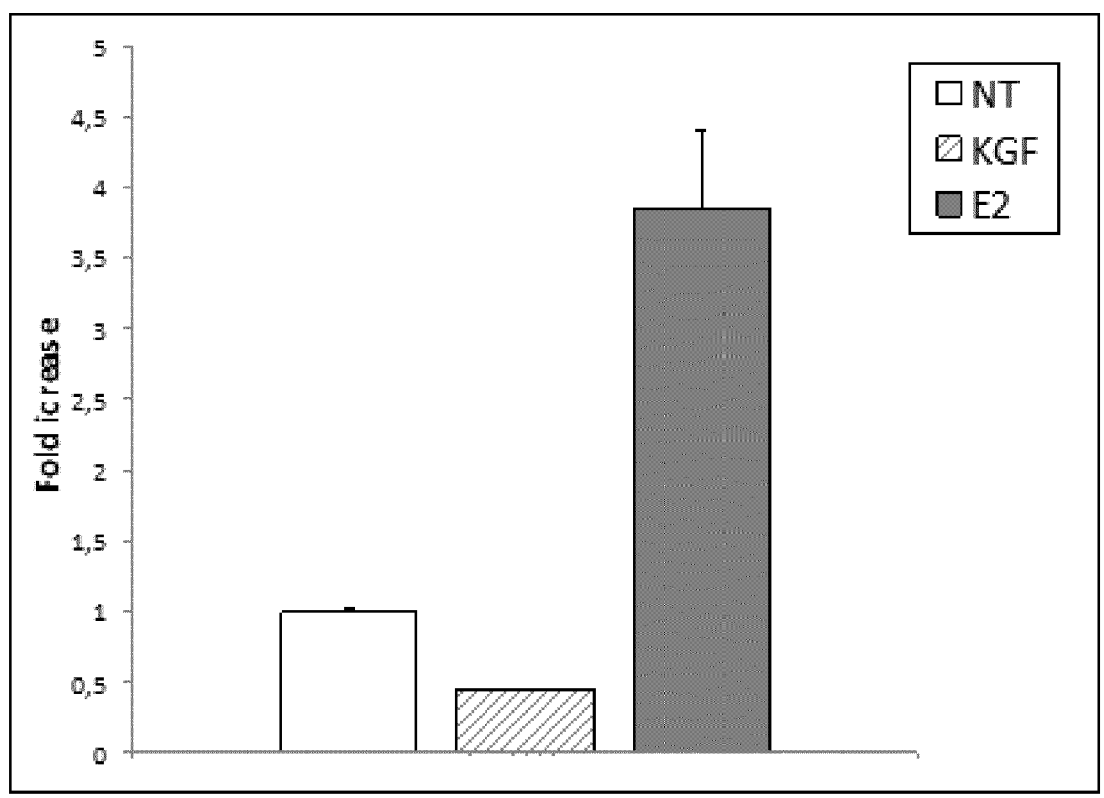
FIG. 5. Role of KGF in the stimulation of the genomic effects of ERalpha. The ERE-LUC construct was transfected into MCF-7 cells treated or untreated with KGF or E2 for 24 h, and the activity of luciferase was determined. Information concerning the luciferase reporter assay was expressed as a rise compared to the control (untreated cells) and represents the average of three separate experiments after the co-reaction for the differences in the efficiency of transfection by means of pRL-TK activity. The error bars represent the standard deviation.

To confirm that KGF acts exclusively by means of the non-genomic pathway, the authors carried out an in vitro transactivation assay with a plasmid containing a sequence of three oestrogen response elements (EREs), DNA sequences to which the ER binds, present on the genes activated by the treatment with oestrogens and bonded to the gene for luciferase. This set of experiments shows that only E2, and not KGF, is able to determine the activation of such a construction, confirming the absence of stimulation of the genomic pathway of the oestrogens on the part of KGF (FIG. 5).

All the indications obtained regarding the in vitro models have therefore supported the initial hypothesis of a use of KGF as an alternative to hormone therapy. In fact, KGF is as active as E2 in the stimulation of the proliferation of the vaginal epithelium, and in addition does not loose its efficacy in the case of co-treatment with tamoxifen. Finally it does not stimulate the genomic pathway of oestrogens, which is the main cause of the systemic effects of treatment with E2 primarily the rise in the incidence of tumours of the breast and endometrium.

Analysis of the Effect of E2 and KGF in an Animal Model of Mice Subjected to Ovariectomy The results obtained in vitro were then transferred in vivo by a study conducted on an animal model, in which the effect of local administration of KGF on vaginal atrophy was assessed. The protocol, which had the approval of the Ministry for Work, Health and Social Politics, Dep. of Public and Veterinary Health, Nutrition and Safety of Diets, Directorate-General of Animal Health and Veterinary Medication, following presentation of the research project for the use of animals in experiments pursuant to Legislative Decree 116/02, was conducted on a base strain CD1 of female mice. To this end, 10 untreated female mice two months old at fertile age were compared with 40 female mice of the same strain and at an age at which they had been subject to an ovariectomy (FIG. 6A).

After 30 days following the ovariectomy, the values of circulating E2 were measured to verify that the were severely decreased in the 40 ovariectomized mice. All the animals enrolled in the study were fed with a special diet devoid of oestrogens (special altromin C1000 phytoestrogen-free diet). The mice subject to an ovariectomy were then divided into groups of 8: one group received no treatment; one group received only the vehicle; one group received the vehicle+E2 30 ng/day; one group received the vehicle+E2 1 μg/day; one group received the vehicle+KGF 10 ng/day; and one group received the vehicle+KGF 30 ng/day.

Assessment of the Efficacy of the Vehicle Used

With the aim of obtaining a single vehicle that allows the release of KGF and of E2, the matrix selected for the study was Pluronic F127, an amphiphilic synthetic block polymer formed from 2 blocks of polyethylene oxide (PEO) spaced by a block of propylene oxide (PPO). This polymer seemed to fit the objective perfectly in as much as it is able to release two different substances: a hydrophilic protein (KGF) and a lipophilic hormone (E2). The polymer, which is already widely used in the biomedical field (healing of wounds, tissue engineering, anti-adhesive in a surgical context) thanks to its biocompatibility, solubilised in water at high concentrations (c≥15% w/v) has the density of a liquid at low temperature, thus making it possible to dilute homogeneously the substances to be used for the treatments, but assumes the density of a hydrogel at greater temperatures (T>25° C.), enabling local application. Before using this substance, the authors carried out a comparative study to verify that the vehicle effect of E2 and KFG, and also their release kinetics in in vivo treatment on the vaginas of mice, was comparable.

To demonstrate the solution-gel transition that occurs with the increase in temperature, the authors carried out a rheological study of a solution of Pluronic F127 (20% weight/volume in $H_2O$), heating the solution at a rate of 2° C./min from 10 to 40° C. and measuring, during this rise in temperature, the G' value (modulus of elasticity) and the G" value (modulus of loss): these parameters describe, respectively, the ability to accumulate and dissipate energy and therefore the resilient or viscous nature of a material. Specifically, a substance in the liquid state is characterised by G" values greater than G' values, and, vice versa, a substance in the gel state has G" values lower than G' values (FIG. 6B). The F127 sample 20% is a solution at T less than 25° C.; between 25 and 28° C. there is a transition of the material, which little by little becomes more elastic before becoming a hydrogel at temperature greater than 28° C. It is therefore possible to store the polymer solution in a refrigerator, to sample it comfortably using a pipette and to then apply it in situ, where it immediately becomes a gel at body temperature.

To compare the release kinetics of both the molecules (KGF and E2), two model molecules were used: myoglobin (MGB), a hydrophilic PM protein comparable to KGF (PMMGB=16700, PMKGF=19000) and prednisolone, a lipophilic hormone characterised by a chemical structure similar to oestradiol (FIG. 6C). The loaded hydrogels were prepared by solubilising at low temperature, in a 5 ml vial, an exact quantity of model molecule (approximately 4-5 mg) in 2 ml of solution of F127 20% w/v; the solution was then brought to the hydrogel state by placing the hermetically sealed vial at 37° C. The vial, closed at the head with a perforated mesh, was then introduced into the release medium (60 ml bidistilled $H_2O$, T=37° C.) and held under constant and gentle stirring. The release therefore occurred by means of diffusion from the upper surface of the gel to the dissolution medium. Periodically, aliquots of the medium (V=2 ml) were removed and substituted with an equal volume of $H_2O$. The release data took into consideration these effects of dilution. The release was almost identical for the two different molecules; this is indicated by the fact that the Pluronic allows the same release typology both for lipophilic molecules and for hydrophilic molecules (FIG. 6D). The release of the model molecules was also almost total within a period of 24 hours.

Figure 7:
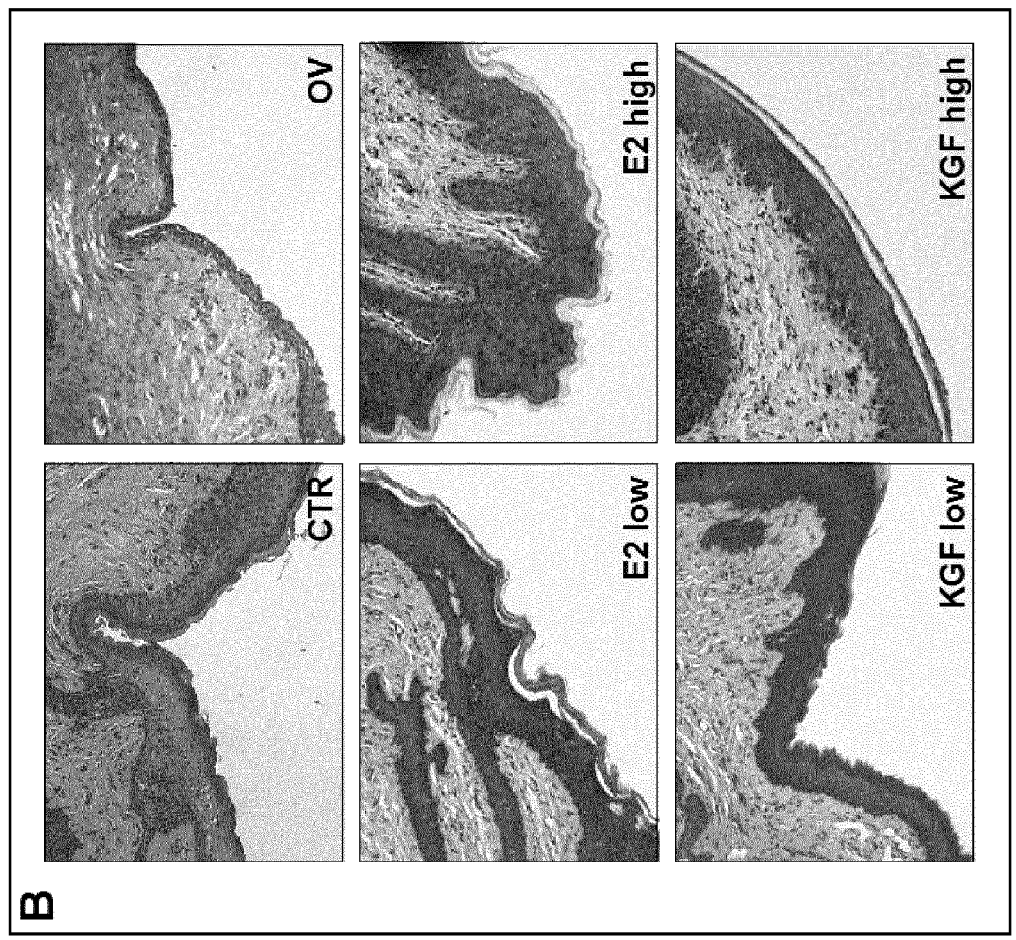
FIG. 7. Assessment of the in vivo effect of KGF and E2 on the vaginal epithelium. (A) Serum concentrations of E2 and KGF in treated rats, measured using the standard ELISA kits for E2 and KGF. The values are expressed in pg/ml, with ND as insignificant average±standard deviation (less than 10 pg/mL). (B) The sections of tissue from the vagina of control mice, mice subject to ovariectomy treated with the only vehicle, and mice treated with low doses and high doses of E2 or KGF were stained with hematoxylin and eosin. The vaginal mucus of control groups shows a stratified squamous epithelium with stratum corneum and the presence of a well-formed stratum lucidum. A significant induction of stratification of the vaginal epithelium and hyperkeratosis is observed in the vagina exposed both to E2 and to KGF (slightly more evident in the groups treated with high doses), but not in the group treated with the only vehicle, in which the vaginal mucus demonstrated a significant reduction of the epithelial thickness compared to the control group (20× enlargement compared to the original).

After daily treatment for 60 days, the animals were killed in order to assess the trophism of the vaginal epithelium after treatment. At the end of the treatment, samples of blood were taken from all the animals in order to assess the serum levels of E2 and KGF. The assessment via ELISA assay made it possible to verify that KGF, not passing the cellular membrane barrier, was not released into the bloodstream, by contrast to E2, which reached the bloodstream even after treatment at low doses (FIG. 7A).

Figure 9:
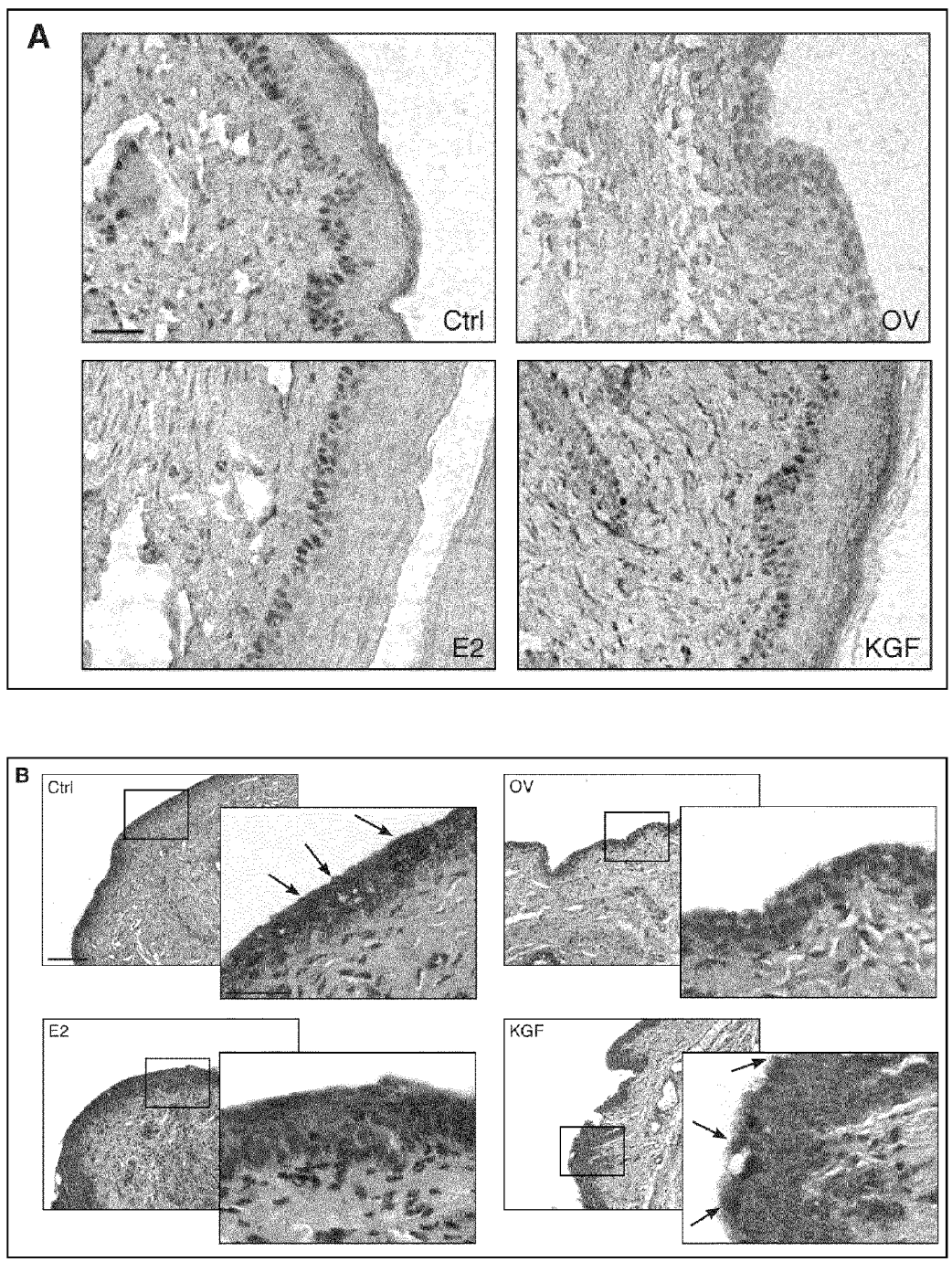
FIG. 9. Assessment of the basal proliferation of the vaginal epithelium after treatment with KGF and E2. (A) Sections of vaginal epithelium were subjected to immunohistochemistry with an anti-PCNA antibody in order to identify the proliferation of the stratum basale. The sections were counterstained with hematoxylin. Sections representative of each treatment group are shown (20× enlargement compared to the original). (B) Tissue sections were subjected to periodic acid-Schiff (PAS) staining procedures. Representative tissue sections for each treatment group are shown (10× enlargement compared to the original). A significant area in each panel is indicated by a square and an enlargement of this area is shown in the overlying panel (40× enlargement compared to the original). Arrows indicates PAS-positive cells.

The animals were killed and the vaginas removed and immediately fixed in formalin and processed for histology. Vaginal epithelium of the treated mice was analysed histologically by means of hematoxylin/eosin and was compared with the epithelium of the group of mice not subjected to ovariectomy (FIGS. 7B and 8A). The criteria adopted in order to determine the trophism of the vaginal mucus were the thickness (evidenced by counting the number of epithelial layers present and by measuring the thickness of the epithelium in μm and also by means of the ratio between area of the epithelial layer and length of the basal membrane) (FIG. 8B) and the proliferative ability of the keratinocytes (determined by means of analyses of the expression of PCNA, a marker of cell proliferation) (FIG. 9).

In conclusion, KGF is very effective both in vitro and in vivo in the stimulation of proliferation of the vaginal epithelium. The authors therefore believe that KGF represents a new possible therapeutic strategy in the treatment of post-menopausal vaginal atrophy that still provides a level of efficacy equal to that of the hormone treatments currently in use, but with reduced risks associated with such treatments.

BIBLIOGRAPHIC REFERENCES

1. Pandit L, Ouslander J G 1997, Am J Med Sci 314:228-231
2. Rossin-Amar B 2000, Gynecol Obstet Feral 28:245-249
3. Santoro N, Komi J 2009, J Sex Med 6:2133-2142
4. Farage M, Maibach H 2006, Arch Gynecol Obstet 273: 195-202
5. Keys H M, et al., 2004, Gynecol Oncol 92:744-751
6. Scholten A N, et al., 2005, Int J Radiat Oncol Biol Phys 63:834-838
7. Lee C M, et al., 2006, JAMA 295:389-397
8. Dickler A, et al., 2010, Radiat Oncol 5:67
9. Grodstein F, et al., 2004, Obstet Gynecol 103:254-260
10. Hendrix S L, et al., 2005, JAMA 293:935-948
11. Colditz G A, et al., 1995, N Engl J Med 332:1589-1593
12. Ross R K, et al., 2000, J Natl Cancer Inst 92:328-332
13. Chlebowski R T, et al., 2010, JAMA 304:1684-1692
14. Trabert B, et al., 2013, Int J Cancer 132:417-426

15. Hall J M, Couse J F, Korach K S 2001, J Biol Chem 276:36869-36872
16. Porter W, Wang F, Wang W, Duan R, Safe S 1996, Mol Endocrinol 10:1371-1378
17. Paech K, et al., 1997, Science 277:1508-1510
18. Cerillo G, et al., 1998, J Steroid Biochem Mol Biol 67:79-88
19. Coleman K M, Smith C L 2001, Front Biosci 6:D1379-D1391
20. Zhou Y, Watters J J, Dorsa D M 1996, Endocrinology 137:2163-2166
21. Watters J J, et al., 1997, Endocrinology 138:4030-4033
22. Singh M 2001, Endocrine 14:407-415
23. Kahlert S, et al., 2000, J Biol Chem 275:18447-18453
24. Shou J, et al., 2004, J Natl Cancer Inst 96:926-935
25. Pancholi S, et al., 2008, Endocr Relat Cancer 15:985-1002
26. Santen R J, et al., 2009, Steroids 74:586-594
27. Bartella V, et al., 2012, Cell Signal 24:1515-1521
28. Finch P W, Rubin J S 2004, Adv Cancer Res 91:69-136
29. Zhang X, et al., 2006, J Biol Chem 281:15694-15700
30. Werner S, et al., 1992, Proc Natl Acad Sci USA 89:6896-6900
31. Marchese C, et al., 1995, J Exp Med 182:1369-1376
32. Brauchle M, et al., 1996, Am J Pathol 149:521-529
33. Werner S 1998, Cytokine Growth Factor Rev 9:153-165
34. Gomperts B N, et al., 2007, Am J Respir Cell Mol Biol 37:48-56
35. Spielberger R, et al., 2004, N Engl J Med 351:2590-2598
36. Beaven A W, Shea T C 2007, Support Cancer Ther 4:188-197
37. Brizel D M, et al., 2008, J Clin Oncol 26:2489-2496
38. Barasch A, Epstein J, Tilashalski K 2009, Biologics 3:111-116
39. Masui F, Matsuda M, Mori T 2004, Cell Tissue Res 318:591-598
40. Panici P B, et al., 2007 Hum Reprod 22:2025-2028
41. Hall J M, McDonnell D P 1999, Endocrinology 140:5566-5578
42. Chambliss K L, et al., 2010, J Clin Invest 120:2319-2330
43. Beral V, et al., 2011, J Natl Cancer Inst 103:296-305
44. Allen N E, et al., 2010, Am J Epidemiol 172:1394-1403
45. Tsilidis K K, et al., 2011, Cancer Causes Control 22:1075-1084.
46. Trabert B, et al., 2012, Br J Cancer 107:1181-1187
47. Furuhjelm M, Karlgren E, Carlström K 1980, Int J Gynaecol Obstet 17:335-339
48. Mattsson L A, Cullberg G, Eriksson O, Knutsson F 1989, Maturitas 11:217-222
49. Willhite L A, O'Connell M B 2001, Pharmacotherapy 21:464-480
50. Johnston S L, et al., 2004, J Obstet Gynaecol Can 26:503-515
51. Ballagh S A 2005, Semin Reprod Med 23:126-140
52. Schiff I, Tulchinsky D, Ryan K J 1977, Fertil Steril 28:1063-1066
53. Martin P L, Yen S S, Burnier A M, Hermann H 1979, JAMA 242:2699-2700
54. Deutsch S, Ossowski R, Benjamin I 1981, Am J Obstet Gynecol 139:967-968
55. Mandel F P, et al., 1983, J Clin Endocrinol Metab 57:133-139
56. Kendall A, Dowsett M, Folkerd E, Smith I 2006 Ann Oncol 17:584-587
57. Bakken K, et al., 2011 Int J Cancer 128:144-156
58. Murkies A L, et al., 1995, Maturitas 21:189-195
59. Dalais F S, et al., 1998, Climacteric 1:124-129
60. Wuttke W, et al., 2002, J Steroid Biochem Mol Biol 83:133-147
61. Nikander E, et al., 2005, Fertil Steril 83:137-142
62. Kaari C, et al., 2006, Maturitas 53:49-58
63. Levis S, et al., 2011, Arch Intern Med 171:1363-1369
64. Kabanov A V, et al., 2002, Adv Drug Deliv Rev 54:223-233
65. Wang Q G, Hughes N, Cartmell S H, Kuiper N J 2010, Eur Cell Mater 19:86-95
66. Nie S, Hsiao W L, Pan W, Yang Z 2011, Int J Nanomedicine 6:151-166
67. Lee Y H, et al., 2012, Exp Diabetes Res 2012:504693
68. Rotolo S, et al., 2008, PLoS One 3:e2528
69. Pandini G, et al., 2007, Cancer Res 67:8932-8941
70. Ignar-Trowbridge D M, et al., 1993, Mol Endocrinol 7:992-998
71. Kato S, et al., 1995, Science 270:1491-1494
72. Bunone G, Briand P A, Miksicek R J, Picard D 1996, EMBO J 15:2174-2183
73. Harrington W R, et al., 2006, Mol Endocrinol 20:491-502
74. Madak-Erdogan Z, et al., 2008, Mol Endocrinol 22:2116-2127
75. Dai R, et al., 2008, Blood 112:4591-4597
76. Wickramasinghe N S, et al., 2009, Nucleic Acids Res 37:2584-2595
77. Murphy A J, Guyre P M, Pioli P A 2010, J Immunol 184:5029-5037
78. Yu X, et al., 2012 BMC Cancer 12:29
79. He Y Q, Sheng J Q, Ling X L, Yen L, Rao J 2012 Exp Mol Med 44:723-732
80. Xu N, et al., 2011, J Invest Dermatol 131:1521-1529
81. Ceccarelli S, et al., 2012, Expert Opin Ther Targets 16:377-393

The invention claimed is:

1. A method of treating a female subject for a condition selected from the group consisting of: vaginal atrophy, dysuria, vaginal pain, vaginal drying and a combination thereof, said condition being caused by a post-menopausal status, by a surgery, or by administering to the female subject a selective estrogen receptor inhibitor, wherein said condition is characterized by thinning and inflammation of the vaginal mucosa,
   (a) wherein the method of treating said condition comprises administering 0.4 micrograms/ml to 1.2 micrograms/ml of a keratinocyte growth factor (KGF/FGF7) to the female subject by a topical or intravaginal route to the female subject's vaginal epithelium,
   (b) wherein the method of (a) induces keratinocyte proliferation, epithelial stratification, and recurrence of mucinous cells in the treated vaginal epithelium of the female subject, and
   (c) wherein the KGF/FGF7 is selected from the group consisting of the amino acid sequence of SEQ ID NO:2, the amino acid sequence of SEQ ID NO:3 and the amino acids 56 to 194 of SEQ ID NO:3.

2. The method according to claim 1, wherein the surgery comprises removal of endometrial cancer.

3. The method according to claim 1, wherein the method further comprises adjuvant vaginal brachytherapy.

4. The method according to claim 1, wherein the selective estrogen receptor modulator is tamoxifen.

5. The method according to claim 2, wherein the endometrial cancer is removed by pelvic or para-aortic lymphadenectomy.

6. A method of treating a condition in a female subject, said condition selected from the group consisting of: vaginal atrophy, dysuria, vaginal pain, vaginal drying and a combination thereof, said condition being induced by administrating tamoxifen to the female subject, wherein said condition is characterized by thinning and inflammation of the vaginal mucosa, the method of treating comprising
   administering to the female subject experiencing said condition 0.4 micrograms/ml to 1.2 micrograms/ml of a keratinocyte growth factor (KGF/FGF7) by a topical or intravaginal route, as needed,
   wherein the KGF/FGF7 is selected from the group consisting of the amino acid sequence of SEQ ID NO:2, the amino acid sequence of SEQ ID NO:3 and the amino acids 56 to 194 of SEQ ID NO:3, and
   wherein said administering of KGF/FGF7 induces keratinocyte proliferation, epithelial stratification, and recurrence of mucinous cells in the treated vaginal epithelium of the female subject.

* * * * *